US007968324B2

(12) United States Patent
Marshall

(10) Patent No.: US 7,968,324 B2
(45) Date of Patent: Jun. 28, 2011

(54) HELICOBACTER SYSTEM AND USES THEREOF

(76) Inventor: Barry J Marshall, Subiaco (AU)

( * ) Notice: Subject to any disclaimer, the term of this patent is extended or adjusted under 35 U.S.C. 154(b) by 247 days.

(21) Appl. No.: 11/202,249

(22) Filed: Aug. 12, 2005

(65) Prior Publication Data

US 2006/0057152 A1 Mar. 16, 2006

Related U.S. Application Data

(60) Provisional application No. 60/602,859, filed on Aug. 20, 2004.

(30) Foreign Application Priority Data

Aug. 13, 2004 (AU) ................................ 2004904564

(51) Int. Cl.
C12N 1/12 (2006.01)
C12N 1/20 (2006.01)

(52) U.S. Cl. .................................. 435/252.1; 435/252.3

(58) Field of Classification Search .......................... None
See application file for complete search history.

(56) References Cited

U.S. PATENT DOCUMENTS

| 5,010,668 | A | | 4/1991 | Zeligson |
| 5,122,457 | A | * | 6/1992 | Reim et al. .................... 435/69.1 |
| 5,403,924 | A | * | 4/1995 | Cover et al. ................... 536/23.1 |
| 5,703,219 | A | * | 12/1997 | Thompson et al. ........... 536/23.2 |
| 5,721,349 | A | | 2/1998 | Cover et al. |
| 5,876,943 | A | * | 3/1999 | Cover et al. ........................ 435/6 |
| 5,877,159 | A | * | 3/1999 | Powell et al. .................... 514/44 |
| 6,027,878 | A | | 2/2000 | Labigne et al. |
| 6,150,170 | A | | 11/2000 | Powell et al. |
| 6,153,390 | A | * | 11/2000 | Cover et al. ........................ 435/6 |
| 6,271,017 | B1 | * | 8/2001 | Labigne et al. .............. 435/252.3 |
| 6,290,962 | B1 | * | 9/2001 | Michetti et al. ............. 424/185.1 |
| 6,383,496 | B1 | | 5/2002 | Curtiss, III et al. |
| 6,410,012 | B1 | | 6/2002 | Sizemore et al. |
| 6,432,680 | B1 | | 8/2002 | Lin et al. |
| 6,531,313 | B1 | | 3/2003 | Goudsmit et al. |
| 6,550,419 | B2 | | 4/2003 | Cohen et al. |
| 6,570,004 | B1 | * | 5/2003 | Blaser et al. .................. 536/23.2 |
| 6,585,975 | B1 | * | 7/2003 | Kleanthous et al. ........ 424/200.1 |
| 6,680,169 | B2 | * | 1/2004 | Morrow et al. .................... 435/5 |
| 6,680,179 | B1 | | 1/2004 | Collins et al. |
| 6,682,729 | B1 | * | 1/2004 | Powell et al. ................. 424/93.2 |
| 6,780,843 | B2 | | 8/2004 | Lin et al. |
| 6,902,903 | B1 | | 6/2005 | Quan et al. |
| 7,129,060 | B1 | * | 10/2006 | Maurer et al. ............... 435/69.1 |
| 7,393,525 | B2 | * | 7/2008 | Powell et al. ................. 424/93.2 |
| 2001/0019834 | A1 | * | 9/2001 | Kim et al. .................... 435/69.2 |
| 2002/0032152 | A1 | | 3/2002 | Torossian |
| 2002/0076417 | A1 | | 6/2002 | Mahan et al. |
| 2002/0161192 | A1 | | 10/2002 | Meyer et al. |
| 2002/0176848 | A1 | | 11/2002 | Sizemore et al. |
| 2002/0192796 | A1 | * | 12/2002 | Legrain et al. .................. 435/219 |
| 2003/0003511 | A1 | * | 1/2003 | Lubitz et al. ..................... 435/7.1 |
| 2003/0023066 | A1 | * | 1/2003 | Haas et al. .................... 536/23.5 |
| 2003/0124141 | A1 | * | 7/2003 | Haas et al. .................... 424/190.1 |
| 2003/0144249 | A1 | * | 7/2003 | Jomaa ............................... 514/79 |
| 2003/0153527 | A1 | * | 8/2003 | Powell et al. .................... 514/44 |
| 2003/0158396 | A1 | * | 8/2003 | Kleanthous et al. ......... 536/23.1 |
| 2003/0170211 | A1 | | 9/2003 | Goudsmit et al. |
| 2003/0170264 | A1 | * | 9/2003 | Turner et al. ............... 424/190.1 |
| 2003/0204068 | A1 | * | 10/2003 | Blaser et al. ................. 536/23.1 |
| 2004/0005325 | A1 | | 1/2004 | Kusters et al. |
| 2004/0043931 | A1 | * | 3/2004 | Hersberg et al. ................ 514/12 |
| 2004/0052799 | A1 | * | 3/2004 | Smith et al. ................. 424/184.1 |
| 2004/0110261 | A1 | | 6/2004 | Hiratsuka et al. |
| 2004/0115669 | A1 | * | 6/2004 | Hiratsuka et al. .................. 435/6 |
| 2004/0203039 | A1 | | 10/2004 | Hensel et al. |
| 2004/0224340 | A1 | * | 11/2004 | Filutowicz ......................... 435/6 |
| 2004/0236072 | A1 | | 11/2004 | Olmsted et al. |
| 2004/0265337 | A1 | | 12/2004 | Zsebo et al. |
| 2004/0266003 | A1 | * | 12/2004 | Powell et al. .................. 435/455 |
| 2005/0075298 | A1 | | 4/2005 | Chen et al. |
| 2005/0096288 | A1 | | 5/2005 | Guevara et al. |
| 2005/0147627 | A1 | * | 7/2005 | Aderem et al. ............. 424/242.1 |
| 2005/0171343 | A1 | * | 8/2005 | Huebner et al. ............. 536/23.7 |
| 2006/0029617 | A1 | * | 2/2006 | Charreyre et al. ......... 424/201.1 |
| 2006/0110408 | A1 | * | 5/2006 | Becker et al. ............... 424/234.1 |
| 2006/0166344 | A1 | * | 7/2006 | Pizza et al. .................... 435/183 |

(Continued)

FOREIGN PATENT DOCUMENTS

WO 96/34631 11/1996

(Continued)

OTHER PUBLICATIONS

Bina, J et al, Journal of Bacteriology, vol. 182(9), May 2000, pp. 2370-2375, Functional expression in *Escherichla coli* and membrane topology of Porin HopE, a member of a Large Family of conserved proteins in *Helicobacter pylori*.*

Josenhans et al, (1998), FEMS Microbiology Letters, vol. 161, pp. 263-273, Green Fluoresent protein as a novel marker and reporter system in *Helicobacter* sp.*

Bina, James, Analysis of the Resistance-Nodulation-Division and Hop Families of Cell Envelope Proteins in *Helicobacter pylori*, Aug. 1998, The University of British Columbia, A Thesis submitted in partial fulfillment of the requirements for the Degree of Doctor of Philosopy, pp. 1-114.*

(Continued)

Primary Examiner — Mark Navarro
(74) Attorney, Agent, or Firm — Fish & Richardson P.C.

(57) ABSTRACT

*Helicobacter* based preparations comprising a pharmacologically active molecule of interest are disclosed, as well as methods of preparing and using said preparations. In particular, *Helicobacter pylori* vectors, vector plasmids and recombinant cells that include a sequence encoding a pharmacologically active molecule of interest useful in therapeutic treatments and/or vaccination against disease are provided. Delivery of the pharmacologically active molecules is provided at the mucosal surface, such as the gastric mucosa or nasal membranes, to provide effective and continuous delivery of a pharmacologically active agent. Vectors and shuttle vector constructs are also provided.

43 Claims, 4 Drawing Sheets

U.S. PATENT DOCUMENTS

| | | | |
|---|---|---|---|
| 2007/0026018 A1* | 2/2007 | Ellis et al. | 424/234.1 |
| 2007/0031382 A1* | 2/2007 | Powell et al. | 424/93.2 |
| 2008/0248068 A1* | 10/2008 | Ljunggren et al. | 424/282.1 |

FOREIGN PATENT DOCUMENTS

| | | | |
|---|---|---|---|
| WO | 98/17804 | * | 4/1998 |
| WO | 98/27819 | * | 7/1998 |
| WO | WO 96/33274 | | 10/1998 |
| WO | WO 99/21959 | | 5/1999 |
| WO | 00/01825 | | 1/2000 |
| WO | 0001825 | * | 1/2000 |
| WO | WO 01/94599 | | 12/2001 |
| WO | 0240516 | * | 3/2002 |
| WO | 0240516 | * | 5/2002 |
| WO | 02/070645 | | 9/2002 |
| WO | WO 2005/021026 | | 3/2005 |

OTHER PUBLICATIONS

Heuermann, D et al, Mol. Gen. Genet. (1998), pp. 519-528, vol. 257, A stable shuttle vector system for efficient genetic complementation of *Helicobacter pylori* strains by transformation and conjugation.*

Kim, Jang Seong et al, Journal of Bacteriology, Nov. 1999, pp. 6969, vol. 181(22), Molecular cloning and Characterization of the *Helicobacter* fliD Gene, an Essential Factor in Flagellar Structure and Motility.*

McGowan, CC et al Molecular Microbiology, vol. 48(5), pp. 1225-1239, Promoter analysis of *Heliocbacter* genes with enhanced expression at low pH.*

Vanet, Anne et al, J. Mol. Biol. (2000), vol. 297, 335-353.*

Panthel, Klau et al, Infection and Immunity, Sep. 2003, pp. 5381-5385, vol. 71(9), Two -components systems of *Helicobacter pylori* contribute to Virulence in a Mouse Infection Model.*

Forsyth, Mark H. et al, Journal of Bacteriology, Apr. 1999, pp. 2261-2266, vol. 181(7), Mutational analysis of the vacA promoter provides insight into gene transcription in *Helicobacter pylori*.*

Fischer, W. et al, Infection and Immunity, Nov. 2001, vol. 69(11), pp. 6769-6775.*

Dietz, P. et al, Journal of Bacteriology, vol. 184(2), pp. 350-362, Jan. 2002.*

Odenbreit, S et al, Science, vol. 287, pp. 1497-1500, 2000.*

Oxer et al, Nucleic Acids Research, vol. 19(11) 1991, pp. 2889-2892, High Level heterologous expression in *E.coli* using the anaerobically activated nirB promoter.*

Bai, et al. "Construction of the attenuated *Salmonella typhimurium* strain expressing *Helicobacter pylori* conservative region of adhesion antigen". Sheng Wu Gong Cheng Xue Bao, vol. 19(4), pp. 433-438, 2003. English Abstract.

Baldari, et al. "Immune subversion by *Helicobacter pylori*". Trends in Immunology. vol. 26, No. 4, pp. 199-207. Apr. 2005.

Choi, et al. "The Role of Ghrelin and Growth Hormone Secetagogues Receptor on Rat Adlpogenesis". Endocrinology vol. 144(3): pp. 754-759, 2003.

Chu, et al. "Patients with *Helicobacter pylori* positive and negative duodenal ulcers have district clinical characteristics". World Journal of Gastroenterology. vol. 11(23): pp. 3518-3522, 2005.

Conway, B.R. "Drug Delivery Strategies For the Treatment of *Helicobacter pylori* Infections". Current Pharmaceutical Design. vol. 11, pp. 775-790, 2005.

Deml, et al. "Characterization of the *Helicobacter pylori* Cysteine-Rich Protein A as a T-Helper Cell Type 1 Polarizing Agent". Infection and Immunity, vol. 73, No. 8, pp. 4732-4742, Aug. 2005.

Forester, et al. "Isolation of *Helicobacter mustelae* from ferrets in New Zealand". New Zealand Veterinary Journal. pp. 65-69, Mar. 2000.

Garborn, et al. "Identification of Novel Virulence-Associated Genes via Genome Analysis of Hypothetical Genes". Infection and Immunity, vol. 72, No. 3, pp. 1333-1340, Mar. 2004.

Graham, et al. "Global Analysis of *Helicobacter pylori* Gene Expression in Human Gastric Mucosa". Gastreonterology. vol. 123, pp. 1637-1648, 2002.

Kang, et al. "Fusion expression of *Helicobacter pylori* neutrophl=activating protein in *E. coli*". World Journal of Gastroenterology, vol. 11, No. 3, pp. 454-456, 2005.

Kong, et al. "Functional analysis of putative restriction-modification system genes in the *Helicobacter pylori* J99 genome". Nucleic Acids Research. vol. 28, No. 17, 2000.

Liu, et al. "Systemic Immune responses to oral administration of recombinant attenuated *Salmonella typhimurium* expresssing *Helicobacter pylori* in mice", World Journal of Gastroenterology, vol. 11, No. 14, pp. 2154-2156, 2005.

Mao, et al. "Construction of hpaA gene from clinical isolate of *Helicobacter pylori* and identification of fusion protein". World Journal of Gastroenterology, vol. 9, No. 7, pp. 1529-1536, 2003.

Moschos, et al. Adjuvant synergy: The effects of nasal coadministrationof adjuvants. Immunology and Cell Biology. vol. 82, pp. 628-637, 2004.

Nolta, et al, "Retroviral-mediated Transfer of the Human Glucocerebrosidase Gene into Cultured Gaucher Bone Marrow". J. Clin. Invest. vol. 90, pp. 342-348, 1992.

Reddy, et al. "Antimicrobal peptides: premises and promises". International Journal of Antimicrobial Agents. vol. 24, pp. 536-547, 2004.

Sawkar, et al, "Chemical chaperones increase the cellular activity of N370S beta-glucosidase: A therapeutic strategy for Gaucher disease". PNAS. vol. 99, pp. 15428-15433, Nov. 14, 2002.

Shi, et al. "Intranasal CpG-Oligodeoxynucleoide is a Potent Adjuvant of Vaccine against *Helicobacter pylori*, and T Helper I Type Response and Interferon-γ Correlate with Protection". Helicobacter. vol. 10, No. 1, pp. 71-79, 2005.

Otto, et al. "The many faces of ghrelin: new perspectives for nutrition research?", British Journal of Nutrition. vol. 93, pp. 765-771, 2005.

Sutton, et al. "Immunisation against *Helicobacter felis* infection protects against the development of gastric MALT Lymphoma", Vaccine. vol. 22, pp. 2541-2546, 2004.

Taschop, et al. "Ghrelin induces adiposity in rodenis", Nature. Vo. 407, pp. 908-913, Oct. 2000.

Velin, et al. "Mast Cells Are Critical Mediators of Vaccine-Induced *Helicobacter* Clearance in the Mouse Model". Gastroenterology. vol. 129: pp. 142-155, 2005.

Jones, et al. "Live attenuated recombinant vaccine protects nonhuman primates against Ebola and Marbung viruses", Nature Medicine. vol. 11, No. 7, Jul. 2005.

Roy Curtiss; "Bacterial Infections Disease Control by Vaccine Development"; *Journal of Clinical Investigation;* vol. 110, No. 8, Oct. 2002; pp. 1061-1066.

J.C. Atherton; "H. Pylori Virulence Factors" *British Medical Bulletin;* vol. 54, No. 1, 1998.

H. Kleanthous et al.; "Characterization of a Plasmid from *Helicobacter pylori* encoding a replication protein common to plasmids in gram-positive bacteria"; *Molecular Microbiology;* Jan. 1991; vol. 5; No. 10 pp. 2377-2389.

Je-Myung Cho, et al.; "Construction of a Shuttle Vector of *Helicobacter pylori* and *Escherichia Coli*"; *Journal of the Korean Society for Microbiology;* vol. 31, No. 5; pp. 557-564.

Paolo Ruggiero et al.; "The Quest for a Vaccine Against *Helicobacter pylori*: How to move from mouse to man"; *Microbes and Infection/ Institut Pasteiur;* Jul. 2003; vol. 5; No. 8 pp. 749-756.

Barry Marshall et al.; "*Helicobacter Pylori* as a Vaccine Delivery System"; *Journal Compilation*; pp. 75-79.

Harborne et al., "Transcriptional control, translation and function of the products of the five open reading frames of the *Escherichia coli nir* operon," Mol. Microbiol., 6:2805-13 (2006) (Abstract only).

* cited by examiner

HELICOBACTER SYSTEM AND USES THEREOF

CROSS REFERENCE TO RELATED APPLICATIONS

This application claims the benefit of U.S. Provisional Application No. 60/602,859, filed Aug. 20, 2004, and to Australian Patent Application No. 2004/904564, filed Aug. 13, 2004, the text of both applications being specifically incorporated herein by reference.

BACKGROUND

1. Field of the Invention

The present invention relates generally to the field of *Helicobacter*-based vector, plasmid vector and shuttle vector systems, as novel *Helicobacter* constructs that include a non-*Helicobacter* pharmacologically active molecule of interest are provided. The invention also relates to the field of drug delivery, vaccines and treatment methods, as compositions that provide for the administration and/or delivery of non-*Helicobacter* molecules at the mucosa in vivo are disclosed.

2. Related Art

*Helicobacter pylori* are a gram-negative spiral shaped bacterium found almost exclusively in the human gastric mucosa. The acidity of the human stomach is an effective barrier to colonization by essentially all bacteria, with the exception of *Helicobacter* species.

*H. pylori* have been described as a causative agent of chronic infection. In particular, *Helicobacter* has been established to play a critical role in peptic ulcer, gastric adenocarcinoma, and primary gastric lymphoma.

*H. pylori* have the unique ability to colonize and persist for decades within the human gastric mucosa, despite development of a mucosal inflammatory and immune response. This characteristic renders *H. pylori* an interesting candidate for the delivery of selected agents though the mucosa. However, this particular application has not found application in mucosal delivery systems in part owing to its involvement in a variety of diseases. A need continues to exist for a delivery system employing these important organisms having a reduced risk of pathology to the host.

The development of mucosal vaccines has also been hindered by the poor immunogenicity of antigens delivered by conventional approaches because of natural barrier functions of the host that prevent access to the mucosal compartment. Hence, a need continues to exist in the medical arts for improved delivery mechanisms for pharmacologically active molecules at the mucosal surface sufficient to elicit a useful and beneficial immunogenic response. Such would provide an effective in vivo delivery system for pharmacological active agents, as well as an effective method for immunization, i.e., antigen exposure at a mucosal surface sufficient to elicit a general humoral and mucosal immune response.

SUMMARY

The present invention is directed to overcoming the above-mentioned challenges and others related to the use of *Helicobacter* and in the treatment of disease. The present invention is exemplified in a number of implementations and applications, some of which are summarized below.

In accordance with some aspects, compositions, methods and systems are provided for preparing and using a *Helicobacter*-based construct comprising a *Helicobacter* sequence having a promoter region and a non-*Helicobacter* sequence encoding a non-*Helicobacter* pharmacologically active molecule. This construct in some embodiments is described as a vector or a plasmid vector, wherein the promoter sequence is capable of controlling the expression of the non-*Helicobacter* pharmacologically active molecule of interest.

In another aspect, a composition comprising a *Helicobacter*-based vaccine is provided. In some embodiments, the *Helicobacter* based vaccine comprises cells transformed with a *Helicobacter* based construct, such as a plasmid vector as described herein. By way of example, the cells transformed with the *Helicobacter* based plasmid vector may comprise *E. coli* cells or *Helicobacter pylori* cells. In some embodiments, the vaccine may be further defined as a live attenuated vaccine.

In some embodiments, the transformed cells are capable of expressing the non-*Helicobacter* pharmacologically active molecule of interest at a mucosal surface.

In other aspects, a recombinant cell is provided comprising cells transformed with the plasmid vectors and/or vectors. In some embodiments, the recombinant cell is capable of secreting the non-*Helicobacter* pharmacologically active molecule of interest at a mucosal surface in an animal. These recombinant cells further comprise, in some embodiments, a secretory sequence and/or a reporter gene sequence. In particular embodiments, the recombinant cell that is transformed is further defined as a recombinant *E. coli* or *H. pylori* cell.

In some aspects, the *Helicobacter*-based vector and vector plasmid constructs comprise a pharmacologically active molecule of interest defined as an antigen, organic or inorganic molecule or substance, a pharmacological agent, e.g. a therapeutic agent or prophylactic agent, such as a gene product or gene sequence (isolated nucleic acid). By way of example, such pharmacologically active molecules of interest may comprise an immunoregulatory agent, hormone, ligand, an enzyme, or an antisense RNA, a catalytic RNA, a protein, peptide or any other molecule. In some embodiments, the isolated nucleic acid molecule may be further described as comprising cDNA, genomic DNA, RNA, or a hybrid molecule thereof. In particular embodiments, the nucleic acid is cDNA By way of example, a protein and/or peptide of interest may comprise ghrelin, amylin, insulin, motilin, β-glucosidase, a chemical chaperone, or other molecule useful in the treatment of Gauchers disease, cell wasting, human immunodeficiency disease (AIDS), appetite suppression, preparations useful in the treatment of diabetes, etc The present invention provides a variety of pharmaceutically acceptable preparations formulated for delivery to a patient, such as, for example, delivery gastrically, orally, or intranasaly. In particular embodiments, the compositions are suitable for delivery at a mucosal surface. In particular embodiments, the composition is suitable for delivery to the mucosal surface of the gut.

By way of example, the mucosa may be that of the gastric, vaginal, nasal, oral, or ocular surface, or any other surface of the body characterized by the presence of a penetrable mucosal surface or lining. In some embodiments, the mucosal surface is the gastric mucosal surface.

The various delivery forms of the compositions are readily prepared for use in the practice of the present invention given the specific types and ratios of specific *Helicobacter*, *Helicobacter* constructs and other delivery vehicles described herein, and those formulation techniques known to those in the formulary arts, such as are described in *Remington's Pharmaceutical Sciences*, 20$^{th}$ edition, Mack Publishing Company, which text is specifically incorporated herein by reference.

It is envisioned that the delivery system may be employed in animals, particularly primates, including humans, equines, bovines, ovines, and rodents, fish and birds. It is also anticipated that the preparations may be used on both infants and adults, as well as parentally or for administration to pregnant or lactating animals. The preparations and methods may be further described as suitable for both male and female animals.

In yet another aspect, a method is provided for vaccinating an animal. In some embodiments, the method comprises administering a composition comprising a vaccine comprising cells transformed with the *Helicobacter*-based vector and/or plasmid vectors as described herein. In other embodiments, the method provides for the delivery of an effective amount of the pharmacologically active molecule of interest sufficient to eliminate or inhibit a disease or physiological condition in the animal, or sufficient to elicit an immune response specific for the pharmacologically active molecule of interest.

By way of example, the non-*Helicobacter* pharmacologically active molecule of interest useful in the vaccine may comprise a mammalian protein, peptide, enzyme, hormone, or any combination of these. In particular embodiments, the pharmacologically active molecule of interest is further defined as a human pharmacologically active molecule of interest. In some embodiments the pharmacologically active molecule of interest is a human pathogen molecule/antigen, human protein antigen, such as amylin or an analog or derivative thereof, or ghrelin, or an analog or derivative thereof.

In particular embodiments, the vaccine conveys immunity against the human pathogen, Ebola virus, HIV virus, Marburg virus, influenza virus, and the like. Replication competent vaccines based on attenuated recombinant vesicular stomatitis virus vectors have been described by Jones et al. (2005)[43] that include Ebola glycoprotein and Marburg glycoprotein. Hence, it is envisioned that constructs using the *Helicobacter*-based vector systems and plasmid vector systems with these and other glycoproteins associated with human pathogens may also be provided according to the present invention together with the disclosure provided herein.

The following nucleic acid and amino acid sequences are referenced throughout the description of the present invention:

SEQ ID NO: 1—Nucleotide sequence of plasmid pHP1 (2796 nucleotides)+ve strand.
SEQ ID NO: 2—Nucleotide sequence of pHP1 (2796 nucleotides)−ve strand.
SEQ ID NO: 3—Nucleotide sequence of plasmid pHP3 (3444 nucleotides).
SEQ ID NO: 4—Hepatitis C virus are antigen (HCV) nucleotide Sequence (580 nucleotides).
SEQ ID NO: 5—Nucleotide sequence 135 bp (45 amino acids) immunogenic coding sequence from the Hepatitis C virus (HCV) core antigen.
SEQ ID NO: 6—Nucleotide sequence (1108 nucleotides) of the surface exposed loop of the HopE gene (at nt504, aa position 168) of *H. pylori*.
SEQ ID NO: 7—Upstream primer (29 nucleotides).
SEQ ID NO: 8—Downstream Primer (28 nucleotides).
SEQ ID NO: 9—Oligonucleotide Primer (15 nucleotides).

BRIEF DESCRIPTION OF THE DRAWINGS

The invention will be described in conjunction with the accompanying drawings, in which.

DETAILED DESCRIPTION

Figure 1:
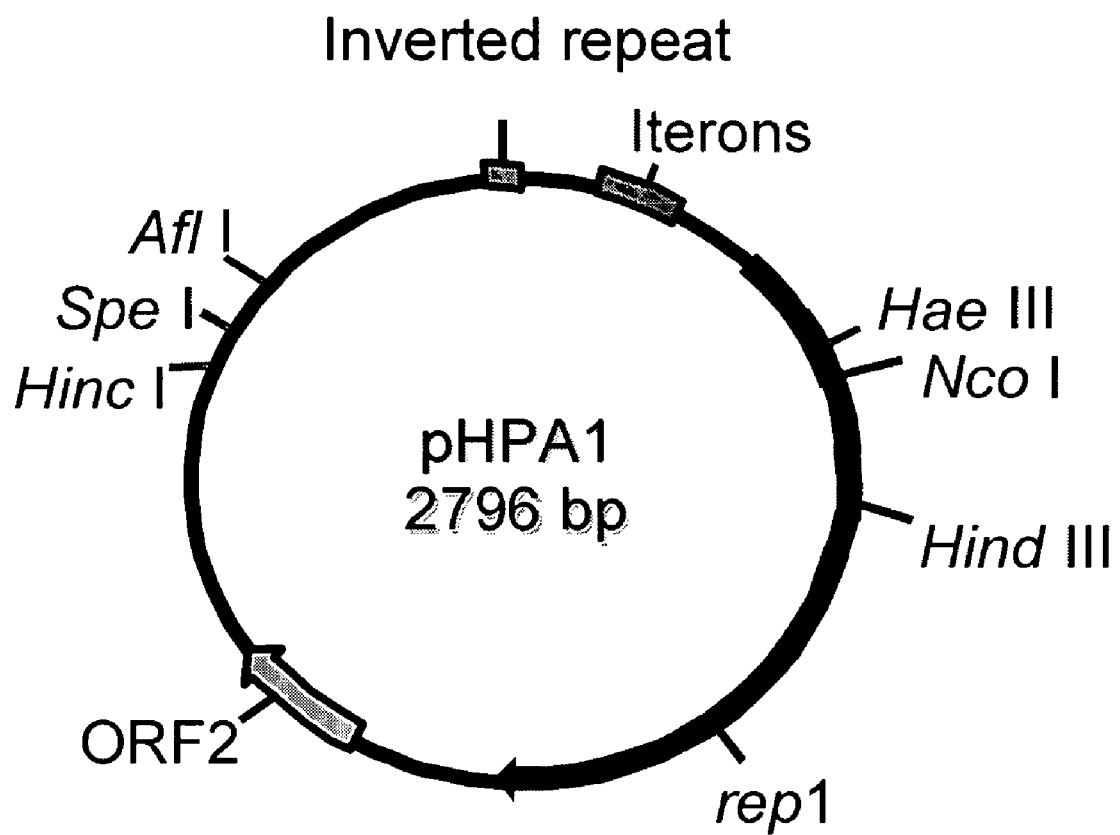
FIG. 1, in accordance with one embodiment of the invention, illustrates the vector constructs, pHPA1 (2.8 kb).

The present invention is believed to be applicable to a variety of different types of bacterial and vaccine constructs that include a *Helicobacter* or *Helicobacter*-based vector system of delivery. It is advantageous to define several terms before describing the invention.

While the present invention is not necessarily limited to such applications, various aspects of the invention may be appreciated through a discussion of various examples using this context.

Description

Before describing the present invention in detail, it is to be understood that this invention is not limited to particularly exemplified methods and may, of course, vary. It is also to be understood that the terminology used herein is for the purpose of describing particular embodiments of the invention only, and is not intended to be limiting which will be limited only by the appended claims.

All publications, patents and patent applications cited herein, whether supra or infra, are hereby incorporated by reference in their entirety. However, publications mentioned herein are cited for the purpose of describing and disclosing the protocols, reagents and vectors which are reported in the publications and which might be used in connection with the invention. Nothing herein is to be construed as an admission that the invention is not entitled to antedate such disclosure by virtue of prior invention.

Furthermore, the practice of the present invention employs, unless otherwise indicated, conventional immunological and molecular biological techniques and pharmacology within the skill of the art. Such techniques are well known to the skilled worker, and are explained fully in the literature. See, e.g., Coligan et al., (*Current Protocols in Protein Science* (1999) Volume I and II (John Wiley & Sons Inc.); Sambrook et al., (*Molecular Cloning: A Laboratory Manual*, 2nd & 3rd Editions. Cold Spring Harbor Laboratory press (1989) (2001); and Bailey, S F. and Ollis, D. F., *Biochemical Engineering, Fundamentals*. McGraw-Hill Book Company, NY, 1986.

It must be noted that as used herein and in the appended claims, the singular forms "a," "an," and "the" include plural reference unless the context clearly dictates otherwise. Thus, for example, a reference to "a nucleic acid" includes a plurality of such nucleic acids, and a reference to "an isolated peptide" is a reference to one or more peptides, and so forth.

Unless defined otherwise, all technical and scientific terms used herein have the same meanings as commonly understood by one of ordinary skill in the art to which this invention belongs. Although any materials and methods similar or equivalent to those described herein can be used to practice the present invention, the preferred materials and methods are now described.

Delivery of therapeutic compositions and nucleic acids to specific target sites within the animal body is an ongoing challenge faced by the drug development industry. The present inventor has developed a *Helicobacter*-based bacterial delivery system capable of carrying vectors encoding biologically active agents, wherein these agents are expressed on the surface of the bacterium or secreted there from. In one embodiment, the bacterium is a species of *Helicobacter*, *H. pylori*. In some embodiments, the strain of *H. pylori* can be any strain known in the field. In some embodiments, the *H. pylori* strain is a non-pathogenic strain such as genomic strain 26695.

In another embodiment, a bacterium, other than *Helicobacter*, is utilized wherein the bacterium has been genetically altered such that it has *Helicobacter* or *H. pylori* features including the ability to chronically colonize the gastric mucosa or other areas of gastrointestinal tract, urinary tract, bronchial epithelium or other mucosal surface, without significant toxicity to the host.

In one embodiment, the *H. pylori* have been manipulated so that some of the pathogenic features have been removed and/or attenuated. For example, the vacuolating cytotoxin and the cag pathogenicity island genes can be removed so that the *H. pylori* are less pathogenic. Attenuating mutations can be introduced into *Helicobacter* using non-specific mutagenesis either chemically, using N-methyl-N-nitro-N-nitrosoquanidine, or using recombinant DNA technologies.

The skilled person will appreciate that the methods of the present invention could be used to deliver biologically active agents. Examples of suitable agents include ones which are capable of functioning locally or systemically, e.g., an agent capable of exerting endocrine activities affecting local or whole-body metabolism and/or an agent which is capable of regulating the activities of cells belonging to the immuno/hematopoeitic system and or an agent which is capable of affecting the viability, growth and differentiation of a variety of normal or neoplastic cells in the body or affecting the immune regulation or induction of acute phase inflammatory responses to injury and infection and/or an agent which is capable of enhancing or inducing resistance to infection of cells and tissues mediated by chemokines acting on their target cell receptors, or the proliferation of epithelial cells or the promotion of wound healing and/or an agent which modulates the expression or production of substances by cells in the body.

Specific examples of such biologically active agents include insulin, growth hormone, prolactin, calcitonin, luteinizing hormone, parathyroid hormone, somatostatin, thyroid stimulating hormone, vasoactive intestinal polypeptide, a structural group I cytokine adopting an antiparallel $4\alpha$ helical bundle structure such as IL-2, IL-3, IL-4, IL-5, IL-6, IL-7, IL-9, IL-10, IL-11, IL-12, IL-13, CM-CSF, M-CSF, SCF, IFN-$\gamma$, EPO, G-CSF, LIF, OSM, CNTF, GH, PRL or IFN $\alpha/\beta$, a structural group 2 cytokine which are often cell-surface associated, form symmetric homotrimers and the subunits take up the conformation of $\beta$-jelly roll described for certain viral coat proteins such as the tumor necrosis factor (TNF) family of cytokines, e.g. TNF $\alpha$, TNF $\beta$, CD40, CD27 or FAS ligands, the IL-1 family of cytokines, the fibroblast growth factor family, the platelet derived growth factors, transforming growth factor $\beta$ and nerve growth factors, a structural group 3 cytokine comprising short chain $\alpha/\beta$ molecules, which are produced as large transmembrane pre-cursor molecules which each contain at least one EGF domain in the extracellular region, e.g., the epidermal growth factor family of cytokines, the chemokines characterized by their possession of amino acid sequences grouped around conserved cysteine residues (the C—C or C—X—C chemokine subgroups) or the insulin related cytokines, a structural group 4 cytokine which exhibit mosaic structures such as the heregulins or neuregulins composed of different domains, e.g., EGF, immunoglobulin-like and kringle domains.

Alternatively, the biologically active agent can be a receptor or antagonist for biologically active agent as defined above.

In some embodiments, the *H. pylori*-based vector and/or vector plasmid construct is employed to create a transformed cell (such as an *E. coli* cell or *Helicobacter* cell) that permits the expression and secretion of a non-*Helicobacter* pharmacologically active molecule of interest at the mucosal membrane of a host to which the transformed cell preparation is administered. The isolated nucleic acid molecule contained within the transformed cell (or vector) may comprise one or more nucleic acid constructs in which nucleic acid encoding the pharmacologically active molecule of interest is under control of *H. pylori* regulatory sequences.

Suitable vectors and shuttle vector sequences can be chosen or constructed to contain appropriate regulatory sequences, including promoter sequences, terminator fragments, enhancer sequences, marker genes and other sequences as appropriate. Vectors may be plasmids, viral, e.g. phage, or phagemid, as appropriate. For further details, for example, see Sambrook et al., supra. Many techniques and protocols are known for the manipulation of nucleic acid, for example in preparation of nucleic acid constructs, mutagenesis, sequencing, introduction of DNA into cells and gene expression, and analysis of proteins, as described in detail in *Short Protocols in Molecular Biology*, Second Edition, Ausubel et al. eds., John Wiley & Sons, 1992. The disclosures of Sambrook et al. supra and Ausubel et al. are incorporated specifically herein by reference.

In some embodiments, the coding sequence(s) for the pharmacologically active molecules of interest is contained in an operon, i.e., a nucleic acid construct for multi-cistronic expression. In an operon, transcription from the promoter results in a mRNA which comprises more than one coding sequence, each with its own suitably positioned ribosome binding site upstream. Thus, more than one agent (pharmacologically active molecule of interest) can be translated from a single mRNA. Use of an operon enables expression of the pharmacologically active molecule of interest to be coordinated.

A nucleic acid construct or vector comprising a coding sequence for a pharmacologically active molecule of interest is preferably under the control of a promoter for expression in *H. pylori*.

In one embodiment, the promoter employed in accordance with the present invention is expressed constitutively in *H. pylori*. Use of a constitutive promoter avoids the need to supply an inducer or other regulatory signal for expression to take place. Preferably, the promoter directs expression at a level at which the *H. pylori* host cell remains viable, i.e., retains some metabolic activity, even if growth may be reduced. Advantageously then, such expression may be at a low level. For example, where the expression product accumulates intracellularly, the level of expression may lead to accumulation of the expression product at less than about 10% of cellular protein, preferably about or less than about 5%, for example about 1-3%.

The promoter may be homologous to the *H. pylori* strain employed, i.e. one found in that strain of *H. pylori* in nature. In some embodiments, the promoter is an arabinose inducible promoter. Other promoters include FlaB sigma 54 promoter (Josenhans et at., 1998, *FEMS Microbiol Lett*, 161(2): 263-73), T7 promoter, and nir B promoter of *Salmonella* (Chatfield et al., 1992, *Biotechnology*, 10(8): 888-92).

In another embodiment the promoter is inducible. Inducible promoters that may be used with clinical grade vectors include, but are not limited to, an inducible promoter as described in U.S. Pat. No. 6,242,194 issued to Kullen et at., a lactose inducible promoter such as that used in *E. coli* plasmids (e.g., pBluescript™ from Stratagene) or the endogenous lactose promoter in *Lactobacillus*, and promoters induced during anaerobic growth, such as the promoter for alcohol dehydrogenase (adhE), as described in Aristarkhov et at., (1999) *J. Bacteriology*, 178(14), 4327-4332).

In one embodiment, the constructs of the present invention also include a toxic gene. These toxic genes are preferably under the control of an inducible promoter so that, on completion of treatment, the *Helicobacter* can be readily eliminated by inducing the expression of the toxic gene. Non-limiting examples of toxic genes include bacterial autolysins under the control of an inducible promoter. The autolysing gene may then be triggered at the appropriate time and place in the gastrointestinal tract through the use of one or more of the inducible promoters as described herein.

In some embodiments, the engineered *Helicobacter* vector and plasmid vector constructs are sensitive to oxygen. This oxygen sensitivity is another method for limiting dissemination of the clinical grade vectors of the present invention. The environment of the human gut is very low in oxygen, suitable for growth of anaerobic and microacrophulic microorganisms, including *Helicobacter*. Thus, an efficient means of eliminating *Helicobacter*, once they have exited the human body upon discharge of intestinal waste into the oxygen-rich outside environment, is to engineer genes into the transformed microorganisms that confer oxygen sensitivity.

The nucleic acid construct or constructs of the present invention may also comprise a secretory signal sequence. Thus, in some embodiments, the nucleic acid encoding the pharmacologically active molecule of interest (for example, a non-*Helicobacter* polypeptide) may provide for secretion of the molecule at a cell membrane by appropriately coupling a nucleic acid sequence encoding a secretory signal sequence to the nucleic acid sequence encoding the molecule (polypeptide). The ability of *Helicobacter* harboring the nucleic acid to secrete the polypeptide may be tested in vitro in culture conditions, which maintain viability of the *Helicobacter*.

Suitable secretory signal sequences include any of those with activity in Gram negative organisms such as *Escherichia*, *Klebsiella* and *Salmonella*. Secretory signal sequences include the *Staphylokinase* enzyme secreted by some strains of *Staphylococcus*, which is known to function in both Gram-positive and Gram-negative hosts (see "Gene Expression Using *Bacillus*", Rapoport (1990), *Current Opinions in Biotechnology*, 1:21-27).

Other secretory signal sequences that can be used include, for example, the β-lactamase gene (Talmadge et at., 1980, *Proc. Natl. Acad. Sci. USA* 77:3369-3373) or the enteroinvasive *E. coli* hemolysin A (hlyA) (Su et at., 1992, *Microbial Pathogen*, 13:465-476). An illustrative list of secretory signal sequences is presented in Pugsley, 1988, Protein secretion across the outer membrane of gram-negative bacteria. In: *Protein Transfer* and *Organelle Biogenesis*, R. C. Dand and P. W. Robbins (eds). Academic Press, Inc., San Diego, pp 607-652.

Selectable markers provide researchers and technicians a convenient means for distinguishing transformed microorganisms from non-transformed ones in a mixed population. One means of identifying transformed organism is to incorporate a selectable marker nucleic acid sequence into the plasmid containing the gene of interest. The selectable marker sequence is generally inserted downstream of the gene of interest and is driven off the same promoter. As a result, cells successfully transformed with the gene of interest will also be transformed with the selectable marker nucleic acid sequence. When antibiotic resistance is used as the selectable marker, only transformed cells will survive and/or grow in media containing the antibiotic.

Thus, antibiotic resistance is a convenient and much used phenotype when developing transformants. However; vectors having antibiotic resistant genes as selective markers are capable of horizontal gene transfer that can endow other organisms with antibiotic-resistant phenotypes. This risk is especially acute when *Helicobacter* is used as part of a therapeutic vector.

In order to use *Helicobacter* as a gene delivery system to animals, the present disclosure presents, in some embodiments, a clinical grade vector system that does not use an antibiotic selection marker. One of the alternatives to using antibiotic resistance genes provided by the present delivery systems includes clinical grade vectors having chromosomal deletions or lethal mutations in a "house-keeping" gene. Next, a functional analogous house-keeping gene is inserted into a plasmid encoding for the pharmacologically active molecule of interest. Consequently, the house-keeping gene becomes the selectable marker allowing for the rapid isolation and identification of transformants.

Examples of "house keeping genes" include genes that encode for any number of metabolic regulators and/or enzymes including, but not limited to kinases, proteases, synthetases, dehydrogenases and others. Another alternative to antibiotic resistance genes provided by the present invention includes clinical grade vectors having reporter genes incorporated into the plasmid containing the gene encoding for the pharmacologically active molecule of interest. Other examples of reporter genes used in accordance with the teachings of the present invention include Green Fluorescent Protein (GFP), β-galactosidase and amylase.

In one embodiment, the pharmacologically active molecule of interest has cytokine activity. Cytokines are discussed in *The Cytokine Facts Rook*, Callard and Gearing (1994), Academic Press. Preferred molecules, such as polypeptides with cytokine activity are interleukins, including Interleukin-2 (IL-2) and Interleukin 6 (IL-6).

In some embodiments, the *Helicobacter* vector and plasmid vector systems comprise a nucleic acid construct as described above that is introduced into a *Helicobacter* or other suitable host cell, to provide transformed cells. Thus, a further aspect provides a method comprising introducing nucleic acid as disclosed into a non-pathogenic *Helicobacter*. Transformation of a culture of host cells, such as *Helicobacter*, may employ any available technique. For *H. pylori* cells, suitable techniques may include calcium chloride transformation, electroporation and transfection using bacteriophage.

The introduction of the plasmid vector into a *Helicobacter* cell may be followed by causing or allowing expression from the nucleic acid, e.g., by culturing *H. pylori* under conditions suitable for expression of the gene. Growing the *Helicobacter* in culture under conditions for expression of the pharmacologically active molecule of interest may be employed to verify that the *Helicobacter* contain the encoding nucleic acid and is able to produce the encoded molecule.

In a further aspect, the present invention provides a method of delivering a therapeutic or prophylactic dose of a biologically active agent in vivo, the method comprising administering to a subject an effective amount of the non-pathogenic preparation of the *H. pylori* compositions and vaccines of the present invention.

It will be appreciated that the methods of the present invention and the use of a non-invasive or non-pathogenic *Helicobacter* as described herein provide a wide range of therapeutic methods which would enable the skilled person to manipulate, for instance, the immune response of a subject. Thus, in one aspect, a method of regulating the survival, growth, differentiation, effector functions or susceptibility to infection of cells or tissues is provided which comprises administering to a subject a non-invasive or non-pathogenic *Helicobacter* as defined herein.

In another aspect, a method of boosting an immune response against tumor cells or an infection colonizing a mucosal surface or adjacent or distant tissue is provided which comprises administering to a subject a non-invasive or non-pathogenic *Helicobacter* as defined herein.

In yet another aspect, a method of modulating the type of immune response (antibody versus cell-mediated) against a pathogenic infectious agent is provided which comprises administering to a subject a non-invasive or non-pathogenic *Helicobacter* as defined herein.

In another aspect, a method of modulating the infiltration of normal tissues with inflammatory or tumor cells is provided which comprises administering to a subject a non-invasive or non-pathogenic *Helicobacter* as defined herein.

In some aspects, a method of controlling the rate of growth, rate of invasion or survival of tumor cells is provided which comprises administering to a subject a non-invasive or non-pathogenic *Helicobacter* as defined herein.

In yet another aspect, a method of inducing apoptosis in tumor cells is provided which comprises administering to a subject a non-invasive or non-pathogenic *Helicobacter* as defined herein.

Other aspects provide for a method of down-regulating an immune response which comprises administering to a subject a non-invasive or non-pathogenic bacterium which expresses a pharmacologically active molecule of interest as defined herein.

In another aspect, a method of treating an allergic autoimmune or other immune dysregulative disease state is provided which comprises administering to a subject a non-invasive or non-pathogenic *Helicobacter* which expresses a pharmacologically active molecule of interest.

The subject can be any primate, equine, bovine, porcine, ovine, rodent, fish, or bird. In one embodiment, the subject is human. Administration may conveniently be nasal or oral.

In a therapeutic context, i.e., where the pharmacologically active molecule of interest is a biologically active agent that provides a beneficial effect to the subject, the amount of the agent and/or treatment regimen will preferably be provided in a "therapeutically effective amount", this being sufficient to show benefit to a subject. Such benefit may be at least amelioration or a reduction in the severity or occurrence of at least one symptom. In a prophylactic context, the amount may be sufficient to reduce the deleterious effect on the subject of a subsequent pathogenic challenge, for instance by enhancing the immune response. The actual amount administered, and rate and time-course of administration will depend on the aim of the administration, e.g., the biological effect sought in view of the nature and severity of the challenge, and is the subject of routine optimization. Prescription of treatment, including prophylactic vaccination, for example, decisions on dosage etc, is within the responsibility of general practitioners and other medical doctors.

A composition comprising *Helicobacter* may be administered in accordance with the present invention alone or in combination with other treatments, either simultaneously or sequentially.

The present invention also provides a pharmaceutical composition comprising a *Helicobacter* as disclosed. Such a pharmaceutical composition is in one embodiment preferably suitable for application to a mucosal membrane.

Pharmaceutical compositions according to the present invention, and for use, may comprise, in addition to the *Helicobacter*, a pharmaceutically acceptable excipient, carrier, buffer, stabilizer or other materials well known to those skilled in the art. Such materials should be non-toxic and should not interfere with the efficacy of the pharmacologically active molecule of interest. The nature of the carrier or other material may depend on the route of administration. For oral administration a parenterally acceptable aqueous solution may be employed which is pyrogen-free and has suitable pH, isotonicity and stability. Those of relevant skill in the art are well able to prepare suitable solutions. Preservatives, stabilizers, buffers, antioxidants and/or other additives may be included, as required. As discussed, a pharmaceutical comprising a *Helicobacter* for administration in accordance with the present invention may comprise one or more nutrient substances, e.g., an energy source such as glucose, amino acids and so on.

In another aspect, a method of manufacture of a pharmaceutical formulations provided comprising formulating *Helicobacter* as disclosed with a suitable carrier medium suitable for administration to an individual. In one embodiment, the pharmaceutical is suitable for application to a mucosal membrane of an individual.

In yet another aspect, a non-pathogenic *Helicobacter* expressing a heterologous pharmacologically active molecule of interest for pharmaceutical use is provided, e.g., for use in a method of treatment of the human or animal body by surgery or therapy, including prophylaxis ("vaccination").

In one embodiment the method can be used to treat, prevent or palliate a disease such as cancer. The methods and delivery system can also be used to treat or prevent a disease or condition of the immune/hematopoietic system, a disease or condition of the reproductive system, a disease or condition of the musculoskeletal system, a disease or condition of the cardiovascular system, a disease or condition described as mixed fetal, a disease or condition of the excretory system, a disease or condition of the neural/sensory system, a disease or condition of the endocrine system, a disease or condition of the respiratory system, a disease or condition of the digestive system and a disease or condition associated with connective/epithelial tissue or disease or condition caused by bacterial, viral or parasitic infection.

In another embodiment, the *Helicobacter* delivery system described herein is capable of concomitant or sequential delivery of a number of different nucleic acid molecules, which encode products capable of treating a number of conditions or diseases described herein. Moreover, preferred delivery systems would also deliver compositions capable of producing additional desirable physiological effects such as appetite suppression or enhancement.

An example of suicide system in *H. pylori* has been described by Panthel et al. 2003 (*Infection & Immunity*, 71: 109-116). This system introduces a plasmid into *H. pylori* which contains the PhiX174 lysis gene E. To eradicate the strain, incubation at 42° C. for 5 hours was used. In vivo this would mean that the animal would consume a drink at 45-50° C. to raise the temperature of the gastric environment above 42° C.

A second example is the L-Dap selection system, commonly used to allow survival of bacterial mutants on supplemented plates (see, for example, Kirata et al. 1997 (Infection & Immunity, 65: 4158-4164)). In this system the animal subject must supplement their diet with a missing substrate i.e., diamino-pimelic-acid (DAP), in order for the DapE deficient *H. pylori* mutant to survive. In order to eradicate the mutants, DAP consumption is ceased.

A third possible system relates to metronidazole sensitivity of *H. pylori* because of its rdxA gene. Excessive replication of the rdxA gene is harmful to mammalian cells and *E. coli*. However, duplication may be tolerated by the bacterium. Therefore a *Helicobacter* species of the present invention can be engineered to contain two copies of rdxA which prevents the normal mutation-dependant rdxA loss. The introduction of at least two functional rdxA genes into the *Helicobacter* genome will result in a *Helicobacter* strain that is permanently sensitive to metronidazole. Jeong et al. 2000 (*J. Bacteriol.*, 182: 5082-5090) showed that the nitroreductase produced by a functional rdxA gene converts metronidazole from a prodrug to a bactericidal compound. The mode of action of the active compound is to cause DNA breaks of the *Helicobacter* genome.

Throughout the specification, unless the context requires otherwise, the word "comprise" or variations such as "comprises" or "comprising", will be understood to imply the inclusion of a stated integer or group of integers but not the exclusion of any other integer or group of integers.

DEFINITIONS

Prior to setting forth the invention, it may be helpful to an understanding thereof to set forth definitions of certain terms that will be used hereinafter.

An "antibiotic resistance gene" as defined herein includes heterologous nucleic acid sequences purposely provided to a vector and used as a selection system. The term "antibiotic resistance gene" does not include other mechanisms or genes that impart antibiotic resistance to naturally occurring microflora organisms.

The term "attenuated" as used herein for example to describe a bacterial strain, particularly an *E. coli* or a *Helicobacter* strain such as *Helicobacter pylori*, is defined as a strain that is less virulent and/or toxic (invasive) that a native, wild type bacterial strain.

The term "biologically active" as used herein refers to ability to perform a biological function and with reference to a polypeptide implies that the polypeptide adopts a stable conformation ("folded form") which is the same or closely analogous to its native conformation. When folded correctly or substantially correctly, for example with formation of proper folded units' α-helices, β-sheets, domains, disulphide bridges etc., a polypeptide should have the ability to perform its natural function. Generally, the unit of function in a polypeptide is a domain.

A "pharmacologically active" molecule of interest, as used in the description of the present invention, is defined as a molecule, such as a peptide, protein, nucleic acid, or other organic or inorganic substance that is capable of eliciting a pharmacologically detectable activity or response in a cell, such as in a cell culture, or in a chemical or biochemical reaction media or assay. These pharmacologically active molecules of interest may thus include biologically active molecules as described herein.

"Clinical grade vector" as used herein means a plasmid or other expression vector that is capable of being expressed in *Helicobacter* or a non-pathogenic bacterium engineered to have features of *Helicobacter*. The clinical grade vectors of the present invention do not use antibiotic resistance markers for selection and/or have been modified to prevent replication outside the host e.g., such as a suicide vector.

"Detectable immune response" as used herein is either an antibody (humoral) or cytotoxic (cellular) response formed in an animal in response to an antigen that can be measured using routine laboratory methods including, but not limited to enzyme-linked immunosorbent assays (ELISA), radio-immune assays (RIA), Enzyme-linked ImmunoSPOT (ELISPOT), immunofluorescence assays (IFA), complement fixation assays (CF), Western Blot (WB) or an equivalent thereto.

"Gene of interest" as used herein refers to any nucleic acid sequence encoding for a pharmacologically active molecule of interest, such as, polypeptide or protein, whose expression is desired. The nucleic acid sequence may or may not include the promoter or other regulatory components. The vectors and plasmid vectors also include constructs capable of producing anti-sense RNA.

"Gene therapy" as used herein is defined as the delivery of a gene of interest to an animal in need thereof using a recombinant vector. The gene of interest can be a transgene encoding for a therapeutic or prophylactic protein or polypeptide including, but not limited to cytokines, anti-inflammatories, anti-proliferatives, antibiotics, metabolic inhibitors/activators and immunologically active antigens and fragments thereof. Furthermore, "gene therapy" as used herein also includes gene replacement technologies directed at both inherited and non-inherited disorders.

The term *Helicobacter* includes all bacteria of the genus *Helicobacter* including *H. pylori* and *Helicobacter mustelae*. The term also includes bacteria that have similar biology to *H. pylori* in that they are capable of residing on the gastric mucosa of primates and/or capable of establishing a chronic, but isolated infection of the mucosa. The term also encompasses bacteria that have been modified so that the bacterium has *H. pylori* features, such as the ability to reside on the gastric mucosa.

A "heterologous" polypeptide is a peptide that is not native or that has been mutated from the native form as it existed in *Helicobacter*, i.e., not expressed by *Helicobacter* in nature or prior to introduction into *Helicobacter*, or an ancestor thereof.

"Host" as used herein defines the intended recipient of a therapeutic composition of the present invention. Host includes all animals. Specifically, hosts include, but are not limited to, primates (including man), bovine, equine, canine, feline, porcine, ovine, rabbits, rodents, birds and fish.

"Immunologically inert" as used herein shall mean any substance, including microorganisms such as microflora that does not provoke a significant immune response in its host. Examples of immunologically inert materials as used herein include stainless steel, biocompatible polymers such as poly-L-lactide, medical grade plastics and the microflora organisms of the present invention.

A "significant immune response" is any immune response that would provide immunity (i.e., invoke the production of specific antibody) in an animal against a given antigenic molecule or immunogen.

An "isolated nucleic acid" is a nucleic acid sequence that is not identical to any naturally occurring nucleic acid or any fragment of a naturally occurring genomic nucleic acid sequence spanning more than three separate genes. The term therefore covers, for example, (a) a DNA molecule which has the sequence of part of a naturally occurring genomic DNA molecule but is not flanked by both of the coding sequences that flank that part of the molecule in the genome of the organism in which it naturally occurs; (b) a nucleic acid incorporated into a vector or into the genomic DNA of a prokaryote or eukaryote in a manner such that the resulting molecule is not identical to any naturally occurring vector or genomic DNA; (c) a separate molecule such as a cDNA, a genomic fragment, a fragment produced by polymerase chain reaction (PCR), or a restriction fragment; and (d) a recombinant nucleotide sequence that is part of a hybrid gene, i.e., a gene encoding a fusion protein.

"Percent identity" (homology) of two amino acid sequences or of two nucleic acids is determined using the algorithm of Karlin and Altschul, 1990, *Proc. Natl. Acad. Sci. USA*. 87:2264-2268, 1990, modified as in Karlin and Altschul (*Proc. Natl. Acad. Sci. USA* 90:5873-5877, 1993). Such an algorithm is incorporated into the NBLAST and XBLAST programs of Altschul et al. (*J. Mol. Biol.* 215:403-410, 1990). BLAST nucleotide searches are performed with the NBLAST program, score=100, wordlength=12, to obtain nucleotide sequences homologous to a nucleic acid molecule of the invention. BLAST protein searches are performed with the XBLAST program, score=50, wordlength=3, to obtain amino acid sequences homologous to a reference polypeptide (e.g., SEQ ID NO: 2). To obtain gapped alignments for comparison purposes, Gapped BLAST is utilized as described in Altschul et al. (*Nucleic Acids Res.* 25:3389-3402, 1997). When utilizing BLAST and Gapped BLAST programs, the default parameters of the respective programs (e.g., XBLAST and NBLAST) are used.

The term "reporter gene" as used herein is a nucleic acid sequence incorporated into (or adjacent to) the heterologous nucleic acid encoding the pharmacologically active molecule of interest that provides the transformed vector expressing the molecule of interest an identifiable phenotype. Non-limiting examples of reporter genes include GFP, β-galactosidase, amylase and CAT.

"Screening marker" as used herein refers to an identifying characteristic (phenotype) provided to a transformed vector made in accordance with the teachings of the present invention. In one embodiment of the present invention, the screening marker is a reporter gene.

"Selectable marker," "selectable gene," "reporter gene" and "reporter marker" (referred to hereinafter as a "selectable marker") as used herein refer to nucleic acid sequences encoding for phenotypic traits that permit the rapid identification and isolation of a transformed bacterial vector. Generally, bacterial vectors deemed "clinical grade" and made in accordance with the teachings of the present invention are those vectors having selectable markers that do not encode for antibiotic resistance.

"Transgene" as used herein refers to a gene that is inserted, using cDNA technology, into a cell in a manner that ensures its function, replication and transmission as a normal gene.

"Transforming nucleic acid sequence" as used herein means a plasmid, or other expression cassette containing a nucleic acid sequence encoding a pharmacologically active molecule of interest. In some embodiments of the present invention, the nucleic acid sequence can encode for one or more therapeutic agents. "Transforming nucleic acid sequence" can also be used to mean a "transgene" in accordance with certain embodiments of the present invention. In another embodiment of the present invention the transforming nucleic acid sequence includes nucleic acid sequence encoding for a promoter and/or other regulatory elements.

The term "cancer" as used herein refers to neoplastic diseases eg., leukemia, cancers and "hyperproliferative disorders"). The neoplasm may be located in a tissue selected from the group consisting of: colon, abdomen, bone, breast, digestive system, liver, pancreas, prostate, peritoneum, lung, blood (e.g., leukemia), endocrine glands (adrenal, parathyroid, pituitary, testicles, ovary, thymus, thyroid), uterus, eye, head and neck, nervous (central and peripheral), lymphatic system, pelvic, skin, soft tissue, spleen, thoracic, and urogenital.

In one embodiment the term "cancer" also encompasses pre-neoplastic conditions selected from the group consisting of hyperplasia (e.g., endometrial hyperplasia), metaplasia (eg, connective tissue metaplasia) and/or dysplasia (e.g., cervical dysplasia, and bronchopulmonary dysplasia).

In another embodiment, the term "cancer" also encompasses benign dysproliferative disorder selected from the group consisting of: benign tumors, fibrocystic conditions, and tissue hypertrophy.

The term "a disease or condition of the immune/hematopoietic system" as used herein refers to a disease or condition selected from the group consisting of: anemia, pancytopenia, leukopenia, thrombocytopenia, leukemia, Hodgkin's disease, non-Hodgkin's lymphoma, acute lymphocytic anemia (ALL), plasmacytomas, multiple myeloma, Burkitt's lymphoma, arthritis, asthma, AIDS, autoimmune disease, rheumatoid arthritis, granulomatous disease, immune deficiency, inflammatory bowel disease, sepsis, neutropenia, neutrophilia, psoriasis, immune reactions to transplanted organs and tissues, systemic lupus erythematosus, hemophilia, hypercoagulation, diabetes mellitus, endocarditis, meningitis, Lyme Disease, Celiac disease (gluten sensitivity) and allergies.

The term "a disease or condition of the reproductive system" as used herein refers to a disease or condition selected from the group consisting of: cryptorchism, prostatitis, inguinal hernia, varicocele, leydig cell tumors, verrucous carcinoma, prostatitis, malacoplakia, Peyronie's disease, penile carcinoma, squamous cell hyperplasia, dysmenorrhea, ovarian adenocareinoma, Turner's syndrome, mucopurulent cervicitis, Sertoli-Leydig tumors, ovarian cancer, uterine cancer, pelvic inflammatory disease, testicular cancer, prostate cancer, Klinefelter's syndrome, Young's syndrome, premature ejaculation, diabetes mellitus, cystic fibrosis, Kartagener's syndrome, testicular atrophy, testicular feminization, anorchia, ectopic testis, epididymitis, orchitis, gonorrhea, syphilis, testicular torsion, vasitis nodosa, germ cell tumors, stromal tumors, dysmenorrhea, retroverted uterus, endometriosis, fibroids, adenomyosis, anovulatory bleeding, amenorrhea, Cushing's syndrome, hydatidiform moles, Asherman's syndrome, premature menopause, precocious puberty, uterine polyps, dysfunctional uterine bleeding, cervicitis, chronic cervicitis, mucopurulent cervicitis, cervical dysplasia, cervical polyps, Nabothian cysts, cervical erosion, cervical incompetence, cervical neoplasms, pseudohermaphroditism, and premenstrual syndrome.

The term "a disease or condition of the musculoskeletal system" as used herein refers to a disease or condition selected from the group consisting of bone cancers (e.g., osteochondromas, benign chondromas, chondroblastoma, chondromyxoid fibromas, osteoid osteomas, giant cell tumors, multiple myeloma, osteosarcomas), Paget's Disease, rheumatoid arthritis, systemic lupus erythematosus, osteomyelitis, Lyme Disease, gout, bursitis, tendonitis, osteoporosis, osteoarthritis, muscular dystrophy, mitochondrial myopathy, cachexia, and multiple sclerosis.

The term "a disease or condition of the cardiovascular system" as used herein refers to a disease or condition selected from the group consisting of: myxomas, fibromas, rhabdomyomas, cardiovascular abnormalities (e.g., congenital heart defects, cerebral arteriovenous malformatiens, septal defects), heart disease (e.g., heart failure, congestive heart disease, arrhythmia, tachycardia, fibrillation, pericardial Disease, endocarditis), cardiac arrest, heart valve disease (e.g., stenosis, regurgitation, prolapse), vascular disease (e.g., hypertension, coronary artery disease, angina, aneurism, arteriosclerosis, peripheral vascular disease), hyponatremia, hypernatremia, hypokalemia, and hyperkalemia.

The term "a disease or condition described as mixed fetal" as used herein refers to a disease or condition selected from the group consisting of: spina bifida, hydranencephaly, neurofibromatosis, fetal alcohol syndrome, diabetes mellitus, PKU, Down's syndrome, Patau syndrome, Edwards syndrome, Turner syndrome, Apert syndrome, Carpenter syndrome, Conradi syndrome, Crouzon syndrome, cutis laxa, Cornelia de Lange syndrome, Ellis-van Creveld syndrome, Holt-Oram syndrome, Kartagener syndrome, Meckel-Gruber syndrome, Noonan syndrome, Pallister-Hall syndrome, Rubinstein-Taybi syndrome, Scimitar syndrome, Smith-Lemli-Opitz syndrome, thrombocytopenia-absent radius (TAR) syndrome, Treacher Collins syndrome, Williams syndrome, Hirschsprung's disease, Meckel's diverticulum, polycystic kidney disease, Turner's syndrome, and gonadal dysgenesis, Klippel-Feil syndrome, Ostogenesis imperfecta, muscular dystrophy, Tay-Sachs disease, Wilm's tumour, neuroblastoma, and retinoblastoma, The term "a disease or condition of the excretory system" as used herein refers to a disease or condition selected from the group consisting of: bladder cancer, prostate cancer, benign prostatic hyperplasia, bladder disorders (e.g., urinary incontinence, urinary retention, urinary obstruction, urinary tract infections, interstitial cystitis, prostatitis, neurogenic bladder, hematuria), renal disorders (e.g., hydronephrosis, proteinuria, renal failure, pyelonephritis, urolithiasis, reflux nephropathy, and unilateral obstructive uropathy).

The term "a disease or condition of the neural/sensory system" as used herein refers to a disease or condition selected from the group consisting of: brain cancer (e.g., brain stem glioma, brain tumors, central nervous system (Primary) lymphoma, central nervous system lymphoma, cerebellar astrocyroma, and cerebral astrocytoma, neurodegenerative disorders (e.g., Alzheimer's Disease. Creutzfeldt-Jakob Disease, Parkinson's Disease, and Idiopathic Presenile Dementia), encephalomyelitis, cerebral malaria, meningitis, metabolic brain diseases (e.g., phenylketonuria and pyruvate carboxylase deficiency), cerebellar ataxia, ataxia telangiectasia, and AIDS Dementia Complex, schizophrenia, attention deficit disorder, hyperactive attention deficit disorder, autism, and obsessive compulsive disorders.

The term "a disease or condition of the respiratory system" as used herein refers to a disease or disorder selected from the group consisting of: cancers of the respiratory system such as larynx cancer, pharynx cancer, trachea cancer, epiglottis cancer, lung cancer, squamous cell carcinomas, small cell (oat cell) carcinomas, large cell carcinomas, adenocarcinomas, allergic reactions, cystic fibrosis, sarcoidosis, histiocytosis X, infiltrative lung diseases (e.g., pulmonary fibrosis and lymphoid interstitial pneumonia), obstructive airway diseases (e.g., asthma, emphysema, chronic or acute bronchitis), occupational lung diseases (e.g., silicosis and asbestosis), pneumonia and pleurisy.

The term "a disease or condition of the endocrine system" as used herein refers to a disease or condition selected from the group consisting of: cancers of endocrine tissues and organs (e.g., cancers of the hypothalamus, pituitary gland, thyroid gland, parathyroid glands, pancreas, adrenal glands, ovaries, and testes), diabetes (e.g., diabetes insipidus, type I and type II diabetes mellitus), obesity, disorders related to pituitary glands (e.g., hyperpituitarism, hypopituitarism, and pituitary dwarfism), hypothyroidism, hyperthyroidism, goiter, reproductive disorders (e.g., male and female infertility), disorders related to adrenal glands (e.g., Addison's Disease, corticosteroid deficiency, and Cushing's Syndrome), kidney cancer (e.g., hypermephroma, transitional cell cancer, and Wilm's tumour), diabetic nephropathy, interstitial nephritis, polycystic kidney disease, glomerulonephritis (e.g., IgM mesangial proliferative glomerulonephritis and glomerulonephritis caused by autoimmune disorders; such as Goodpasture's syndrome), and nephrocalcinosis.

The term "a disease or condition of the digestive system" as used herein refers to a disease or condition selected from the group consisting of: ulcerative colitis, appendicitis, Crohn's disease, hepatitis, hepatic encephalopathy, portal hypertension, cholelithiasis, cancer of the digestive system (e.g., biliary tract cancer, stomach cancer, colon cancer, gastric cancer, pancreatic cancer, cancer of the bile duct, tumors of the colon (e.g., polyps or cancers), and cirrhosis), pancreatitis, ulcerative disease, pyloric stenosis, gastroenteritis, gastritis, gastric atrophy, benign tumors of the duodenum, distension, irritable bowel syndrome, malabsorption, congenital disorders of the small intestine, bacterial and parasitic infection, megacolon, Hirschsprung's disease, aganglionic megacolon, acquired megacolon, colitis, anorectal disorders (e.g., anal fistulas, hemorrhoids), congenital disorders of the liver (e.g., Wilson's disease, hemochromatosis, cystic fibrosis, biliary atresia, and alpha 1-antitrypsin deficiency), portal hypertension, cholelithiasis, and jaundice.

The term "a disease or condition of the connective/epithelial" as used herein refers to a disease or condition selected from the group consisting of: connective tissue metaplasia, mixed connective tissue disease, focal epithelial hyperplasia, epithelial metaplasia, mucoepithelial dysplasia, graft v. host disease, polymyositis, cystic hyperplasia, cerebral dysplasia, tissue hypertrophy, Alzheimer's disease, lymphoproliferative disorder, Waldenstron's macroglobulinemia, Crohn's disease, pernicious anemia, idiopathic Addison's disease, glomerulonephritis, bullous pemphigoid, Sjogren's syndrome, diabetes mellitus, cystic fibrosis, osteoblastoma, osteoclastoma, osteosarcoma, chondrosarcoma, osteoporosis, osteocarthritis, periodontal disease, wound healing, relapsing polychondritis, vasculitis, polyarteritis nodosa, Wegener's granulomatosis, cellulitis, rheumatoid arthritis, psoriatic arthritis, discoid lupus erythematosus, systemic lupus erythematosus, scleroderma. CREST syndrome, polymyositis, dermatomyositis, mixed connective tissue disease, relapsing polychondritis, vasculitis, Henoch-Schonlein syndrome, erythema nodosum, polyarteritis nodosa, temporal (giant cell) arteritis, Takayasu's arteritis, Wegener's granulomatosis, Reiter's syndrome, Behcet's syndrome, ankylosing spondylitis, cellulitis, keloids, Ehler Danlos syndrome, Marfan syndrome, pseudoxanthoma elasticum, osteogenesis imperfecta, chondrodysplasias, epidermolysis bullosa. Alport syndrome and cutis laxa.

The term "a" and "the" as used in the present descriptive is intended to include both one (the singular) and more than one (plural).

A "therapeutically effective amount" of a pharmacologically active molecule of interest or combination of said molecules as described herein is understood to comprise an amount effective to elicit the desired response but insufficient to cause a toxic reaction. A desired response, for example, may constitute the formation of a sufficient and/or acceptable detectable antibody titer level in a blood sample. The dosage and duration of treatment of the preparation to be administered to a subject will be determined by the health professional attending the subject in need of treatment, and will consider the age, sex, weight, extent of existing diseased state and/or tissue damage of the subject, and specific formulation of *Helicobacter* and the gene of interest product being used as the treatment for the subject.

The phrase, "effective level" refers to the level of the desired activity of the pharmacologically active molecule of interest and not necessarily limited to the number of molecules. For example, the effective level of amylin (as an exemplary pharmacologically active molecule of interest) may be decreased to stimulate ghrelin secretion by using amylin antagonists, without a necessary concomitant decrease in the amount of free amylin present in a subject.

The phrase "ghrelin-associated diseases and disorders" refers to any condition that can be treated prevented or ameliorated through the modulation of ghrelin activity. These include conditions that are enhanced, exacerbated or stimulated by ghrelin, for example, growth hormone release or drive to eat. The physiological actions of ghrelin are considered to include, by way of example, the stimulation of growth hormone release, the stimulation of hormone secretion from lactotrophs and corticotropes, orexigenic and cardiovascular actions, anti-proliferative effects on thyroid and breast tumors and regulation of gastric motility and acid secretion through vagal mediation. (See WO 2005021026).

Where the definition of terms departs from the commonly used meaning of the term, applicant intends to utilize the definitions provided herein, unless specifically indicated.

The invention will now be further described by reference only to the following non-limiting examples. It should be understood, however, that the examples following are illustrative, and should not be taken in any way as a restriction on the generality of the invention described herein. In particular, while the invention is described in detail in relation to the use of a specific *H. pylori* strain, it will be clearly understood that the findings herein are not limited to this strain.

Example 1

Vectors and Transgenic *H. Pylori* Organisms for Stable Expression of Foreign Proteins The genetic manipulation of *H. pylori* is uncommon. The present example demonstrates the utility of the invention for providing a genetically transformed *Helicobacter*, particularly transformed *H. pylori*. The transformed bacterium are prepared using plasmids and plasmid vectors derived from *Helicobacter*, which have had been subject to prior manipulation in a non-*Helicobacter* organism, such as *E. coli*.

Several *H. pylori* plasmids described in the literature can be successfully converted to *H. pylori/E. coli* shuttle vectors. Many strains of *E. coli* have been reported to be naturally competent for DNA uptake. Resistance markers for streptomycin, rifampin and metronidazole have also been successfully transformed into most strains of *H. pylori*. However, while plasmid DNA from *E. coli* and other organisms can be introduced into *H. pylori*, these plasmids cannot be stably maintained. Moreover, *H. pylori* plasmids cannot be transformed into *E. coli* or *Helicobacter* species. Accordingly, *H. pylori* shuttle vectors must be constructed.

Figure 2:
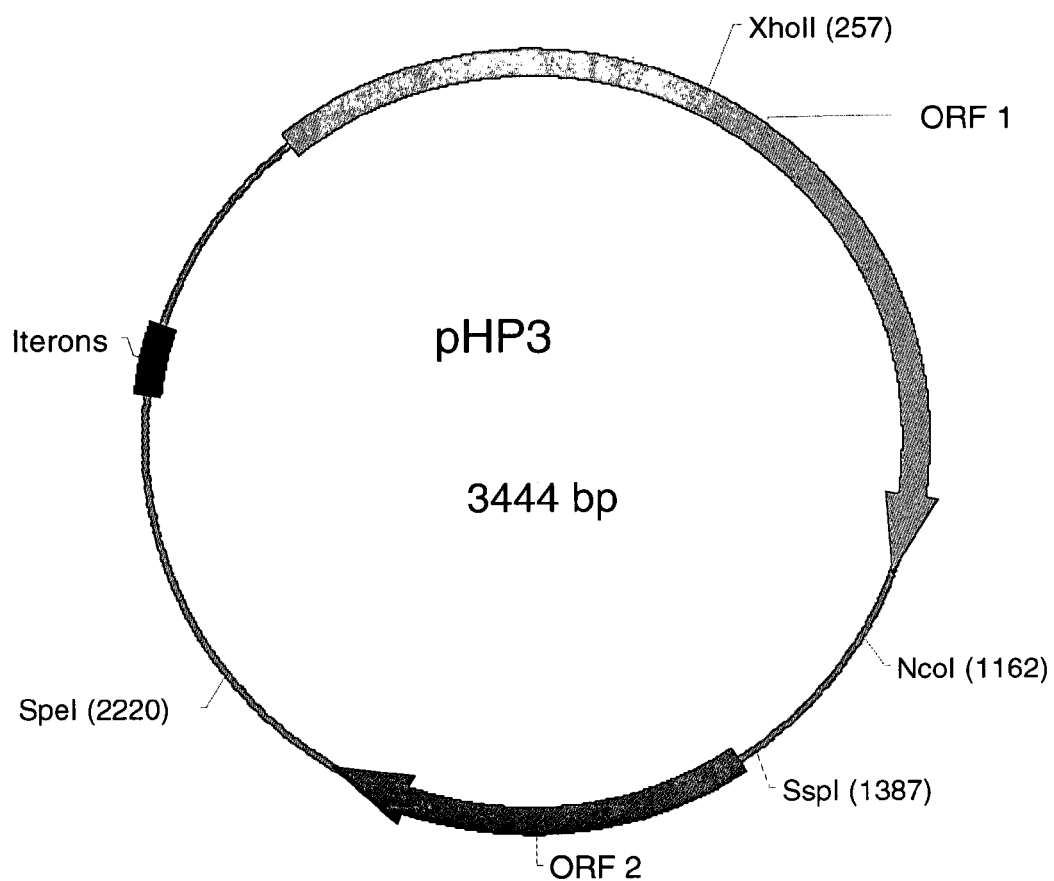
FIG. 2, in accordance with one embodiment of the invention, presents a schematic diagram of the plasmid construct pHP3 (3.4 kb).

Two plasmids from *H. pylori* are illustrated in the schematics shown in FIGS. 1 and 2. Vectors pHPAI (2.8 kb) (FIG. 1) and pHP3 (3.4 kb) (FIG. 2) have been sequenced, and it has been revealed that pHPAI replicated via the theta mode of plasmid replication. In contrast to rolling-circle replicating plasmids, theta plasmids do not generate single-stranded DNA intermediates during replication and are thus more stable vector candidates because they are less prone to illegitimate recombination. Furthermore, the pHPAI origin of replication (ori) contains a series of direct repeat sequences (termed "iterons") that are involved in replication control and maintaining stable copy number. Vector pHP3 shares many of these features. The nucleotide sequences for these two vectors are shown below.

Plasmid pHP1 shown in double stranded form (top strand is (+ strand) SEQ ID: 1; bottom strand is (− strand) (SEQ ID NO: 2)

```
GTCATGCGCGTTGTTTTAATTACATTTTAAACAACTTGTTGTTGTTTTACATGTTTTACTCGC    65
CAGTACGCGCAACAAAAATTAATGTAAAATTTGTTGAACAACAACAAAAATGTACAAAATGAGCG

ATGCGCGCGCGTGAGGGATTGGGGGTTGCAACCCCCTAAATAACGAAGCTGTAGGGTTTCTCATT   130
TACGCGCGCGCACTCCCTAACCCCCAACGTTGGGGGATTTATTGCTTCGACATCCCAAAGAGTAA

TTTGTGGTGAAAATGAATAAAACAGAACTTCTTGCCAACACTAACAGAACTTCTTGCCAACACTA   195
AAACACCACTTTTACTTATTTTGTCTTGAAGAACGGTTGTGATTGTCTTGAAGAACGGTTGTGAT

ACAGAACTTCTTGCCAACACTAACAGAACTTCTTGCCAACACTAACAGAACTTCTTTATTTTAAA   260
TGTCTTGAAGAACGGTTGTGATTGTCTTGAAGAACGGTTGTGATTGTCTTGAAGAAATAAAATTT

GTTATGATTATTAACAATTTTTAGACATAATAACAGCGTGTGAAGATACTTTTGTAGCGGTATTT   325
CAATACTAATAATTGTTAAAAATCTGTATTATTGTCGCACACTTCTATGAAAACATCGCCATAAA

CCTATGTGCGGCAAAATTTGGAGCAATTAGCTTGACTTGGTTGAGTTAGTGGGTTGGAGGATAGA   390
GGATACACGCCGTTTTAAACCTCGTTAATCGAACTGAACCAACTCAATCACCCAACCTCCTATCT

GAGGGCGACACCTCGTTAGGAGGTATCAATGTGAAAGTATTTGTCGTATTAGTTCTAGTATTAGT   455
CTCCCGCTGTGGAGCAATCCTCCATAGTTACACTTTCATAAACAGCATAATCAAGATCATAATCA

AATTCTCGCACAATTGCTATATTAGGCTTATTCGTGGTCTAACCCCTTGTTTATGGGGGTTGGCT   520
TTAAGAGCGTGTTAACGATATAATCCGAATAAGCACCAGATTGGGGAACAAATACCCCCAACCGA

CGTTATAAGCATACTGATACGATCACACTTATTATACACCAAAAGATAAGGAGTATAGAGTGGAA   585
GCAATATTCGTATGACTATGCTAGTGTGAATAATATGTGGTTTTCTATTCCTCATATCTCACCTT

TTTGATCAATCAGATTTACAAAAAGCGTTGAAAATATTAGATACACTCCCACAAACCCCACAAAT   650
AAACTAGTTAGTCTAAATGTTTTTCGCAACTTTTATAATCTATGTGAGGGTGTTTGGGGTGTTTA

TGAGCTACAAAAACAAGAAATACAAAACCGCATCAACAAAATAACAGAGACAATCATTAAAGAAT   715
ACTCGATGTTTTTGTTCTTTATGTTTTGGCGTAGTTGTTTTATTGTCTCTGTTAGTAATTTCTTA
```

-continued

```
TACTATCAAAGCATGAAATCAAGAAAGAAGAACTAGAACCCACTCTAACCCCAAAACCCACACCA         780
ATGATAGTTTCGTACTTTAGTTCTTTCTTCTTGATCTTGGGTGAGATTGGGGTTTTGGGTGTGGT

CTCAAAGAGCCACAAACCACCCCAACACCATGCAAAGATTTAGTGGTTAGCACCCCTAAAGATAA         845
GAGTTTCTCGGTGTTTGGTGGGGTTGTGGTACGTTTCTAAATCACCAATCGTGGGGATTTCTATT

AACCTAATATCACCTACCACAATAACGCTAATAAGGTCAATCTAGGGAAATTGAGCGAAAGGGAA         910
TTGGATTATAGTGGATGGTGTTATTGCGATTATTCCAGTTAGATCCCTTTAACTCGCTTTCCCTT

GCCAATCTTTTATTCGCTATTTTTCAAAAACTCAAAGCCCAAGGGAATACCCTCATTCGTTTTGA         975
CGGTTAGAAAATAAGCGATAAAAAGTTTTTGAGTTTCGGGTTCCCTTATGGGAGTAAGCAAAACT

ACCGCAAGATTTGAAACGCATGCTAAACATAGATATTTCTAATGAGCGCTTATCAGAAGTCGTTA        1040
TGGCGTTCTAAACTTTGCGTACGATTTGTATCTATAAAGATTACTCGCGAATAGTCTTCAGCAAT

TTAAGCTGTGGGATAGCATTAAAACCGCTGATTTTTGGAAAATTAGCGAAACCGAAACTTCAATC        1105
AATTCGACACCCTATCGTAATTTTGGCGACTAAAAACCTTTTAATCGCTTTGGCTTTGAAGTTAG

ATTCAAGAAAATTACATGCTTTTTAGTCGGTGTAAAATTGAATTGAACAAACCGAGTAAAGATTT        1170
TAAGTTCTTTTAATGTACGAAAAATCAGCCACATTTTAACTTAACTTGTTTGGCTCATTTCTAAA

GAAGTATTTAGAAATCCAACTCAACGATAACTATCAAGACTTACTCAACAATCTGGGCATGGGTC        1235
CTTCATAAATCTTTAGGTTGAGTTGCTATTGATAGTTCTGAATGAGTTGTTAGACCCGTACCCAG

AATACACTTCTTTCAATCTGTTAGAATTTCAAAGAGTGAGGGGTAAATACGCTAAAACGCTCTAT        1300
TTATGTGAAGAAAGTTAGACAATCTTAAAGTTTCTCACTCCCATTTATGCGATTTTGCGAGATA

CGCTTGCTCAAGCAATACAAAAGCACAGGGATTTTGAGCGTGGAATGGACTCAATTCAGGGAGCT        1365
GCGAACGAGTTCGTTATGTTTTCGTGTCCCTAAAACTCGCACCTTACCTGAGTTAAGTCCCTCGA

TTTAGACATTCCAAAAGACTACAAAATGGAAAACATCGATCAAAAAGTCTTAACCCCCTCTCTCA        1430
AAATCTGTAAGGTTTTCTGATGTTTTACCTTTTGTAGCTAGTTTTTCAGAATTGGGGGAGAGAGT

AAGAACTCAGAAAAATCTACCCTTTTGAACACTTGAGCTATAAAAAAGAACGCAAAAGCCATTAC        1495
TTCTTGAGTCTTTTTAGATGGGAAAACTTGTGAACTCGATATTTTTTCTTGCGTTTTCGGTAATG

AAGCGCAAAGTAACCCACATTGATTTTTATTTTGAGCAATTTCCTTAAGGCGAAAATAAGAAACA        1560
TTCGCGTTTCATTGGGTGTAACTAAAAATAAAACTCGTTAAAGGAATTCCGCTTTTATTCTTTGT

AAACAAAGCCGACAAGCAACGCGCTCAAAGGGACATCAAGCTTGTAGCATGGGATATTCACAACC        1625
TTTGTTTCGGCTGTTCGTTGCGCGAGTTTCCCTGTAGTTCGAACATCGTACCCTATAAGTGTTGG

AAATCGCTAAAAGAAACGCAAAAGCCACTATGGAAGCTAGGTTTCTTGAATTGAAAACTTTGATC        1690
TTTAGCGATTTTCTTTGCGTTTTCGGTGATACCTTCGATCCAAAGAACTTAACTTTTGAAACTAG

GGCTATCAGTTCAGGAACAATGACAGTAGGAACAAATTAAAGATTGACAACACCACTTTTGAAAG        1755
CCGATAGTCAAGTCCTTGTTACTGTCATCCTTGTTTAATTTCTAACTGTTGTGGTGAAAACTTTC

AATCAAATGTATTTACATGTATCTTAACCCTAAAAATAAGCATAACCCCCAAAAATTCCTTGTAT        1820
TTAGTTTACATAAATGTACATAGAATTGGGATTTTTATTCGTATTGGGGGTTTTTAAGGAACATA

CCAACAAGACATTCGCATTGGAACTACTATATATCAATAGATACAGCCTAAAAAAAAGACAACTT        1885
GGTTGTTCTGTAAGCGTAACCTTGATGATATATAGTTATCTATGTCGGATTTTTTTTCTGTTGAA

GCTAGAAGAATTTAACCCCCCAAAATCCACCCTATCACCAACGAACCTATCAAGGAATTTGCAGA        1950
CGATCTTCTTAAATTGGGGGGTTTTAGGTGGGATAGTGGTTGCTTGGATAGTTCCTTAAACGTCT

ATACATCGGCAAAACGATTAACATCACCAACTTCAATGTGGATCAATGCCATGAGGGAATCAGCA        2015
TATGTAGCCGTTTTGCTAATTGTAGTGGTTGAAGTTACACCTAGTTACGGTACTCCCTTAGTCGT

ACTACCTGACAATCACTAGGATCGTGAACTGGACGTAATCGGATCTGTATTTGGTCCAGATGTGG        2080
TGATGGACTGTTAGTGATCCTAGCACTTGACCTGCATTAGCCTAGACATAAACCAGGTCTACACC

ATAAGCCTGGGACTTCTCAAGCCTTTCATTGCTAAAGTGAGAAAATTTGGGGATTGGTTCAAGAA        2145
TATTCGGACCCTGAAGAGTTCGGAAAGTAACGATTTCACTCTTTTAAACCCCTAACCAAGTTCTT

CACTACAGGTGAAAAGACAGATGCATGCTGACTAAACTCATAGAAAAACTGAATCACGAAAGAAA        2210
GTGATGTCCACTTTTCTGTCTACGTACGACTGATTTGAGTATCTTTTTGACTTAGTGCTTTCTTT

GAATGCAAGCAGAAAACAAACACCTAAAAGAACAAGGACTAGAAAAAATCTACACTCAAAAAGAC        2275
CTTACGTTCGTCTTTTGTTTGTGGATTTTCTTGTTCCTGATCTTTTTAGATGTGAGTTTTTCTG

TACGAGCAGTTAAAAGAACAGCATTTGAAAGAAATTGAAGCACTCAAAAAAGAAATCCAAAAAAC        2340
ATGCTCGTCAATTTTCTTGTCGTAAACTTTCTTTAACTTCGTGAGTTTTTTCTTTAGGTTTTTTG

CAAGCAAGAAACATACACGCAACCAAAAGAATGTAGCCATTTAGCGCATTCTTTTAGCCCTAATT        2405
GTTCGTTCTTTGTATGTGCGTTGGTTTTCTTACATCGGTAAATCGCGTAAGAAAATCGGGATTAA

CATTCTTTCAATCAAAATCCGACTAATTCATCGGCTAAACGCTAAAAATCGCTTAAAACGAAAAA        2470
GTAAGAAAGTTAGTTTTAGGCTGATTAAGTAGCCGATTTGCGATTTTTAGCGAATTTTGCTTTTT
```

```
                                                   -continued
TACAAAGCAAAAAACTTCATTCCCCTTTTAGTCGTTAACCATTTAGCCAATCTAACTAGTTTAGC    2535
ATGTTTCGTTTTTTGAAGTAAGGGGAAAATCAGCAATTGGTAAATCGGTTAGATTGATCAAATCG ATCTAAAGGCGAATCTATCTTGTGTTAGACATCCAACCTTACCAAAACCGCAGAGCGAGCTTAAG    2600
TAGATTTCCGCTTAGATAGAACACAATCTGTAGGTTGGAATGGTTTTGGCGTCTCGCTCGAATTC AGAGATTCAAGCGGTTTTGCACGATTGTTTGCTGCCAAGAAAACCAACAAGCGAAGTAAGGCGCA    2665
TCTCTAAGTTCGCCAAAACGTGCTAACAAACGACGGTTCTTTTGGTTGTTCGCTTCATTCCGCGT TAGACAAAAGCGCATCGCAGTTTGAAAGCGTAGGCGTCAGAAGTGGTTTGCGTTAGAATCAAACA    2730
ATCTGTTTTCGCGTAGCGTCAAACTTTCGCATCCGCAGTCTTCACCAAACGCAATCTTAGTTTGT AGATAGCGCAAACCTGGCGTTAGGCTAAAAAACCCCTAAAAACTAAAACCCCAAAATATGTAGTGC    2796
TCTATCGCGTTTGGACCGCAATCCGATTTTTTGGGGATTTTTGATTTTGGGGTTTTATACATCACG
```

Plasmid pHP3 shown in single stranded form (SEQ ID NO: 3):

```
TCTACACAATTAACAATCTTTAGCTACAATAACAGCGTGTGAAGATGCTTTCACAGCGGT        60

ATTTCCTATGTGCGGCAAAATTTGGAGCAATTAACTTGACTTGGTTGGGTTAGTGGGTTG       120

GAGGATAGAGAGGGCGACACCTCGTTAGGAGGTATCAATGTGAAAGTATTTGTCGTATTA       180

GTTCTAGTATTAGTAATTCTCGCACAATTGCTATATTAGGCTTATTTGTGGTCTAACCCC       240

TTGTTTATGGGGGTTAGATCCTTATAAGCATACTGATACGATCACACTTATTATACACCA       300

AAAGATAAGGAGTATAGAGTGGAATTTGATCAATTAGAATCACAAAGATCAGACTTACAA       360

AAAGTGTTAAAAGAATTAGATACACTCCCAAAAACCCCACAAATTGAGCTACAAAAACAA       420

GAAATACAAAACCGCATCAACAAAATAACAGACACAATCATTAAAGAATTACTATCAAAA       480

CATGAAATCAAAAAGAAGAACTAGAACCCACTCTAACCCCAAAACCCACACCAACAAAA        540

GAGCCACAAACCACCCCCACACCATGCAAAAATTTAGTGGTTAGCACCCCTAAAGATAAA       600

ACCTATATCACCTACCACAATAACGCTAATAAGGTCAATCTAGGGAAATTGAGCGAAAGG       660

GAAGCCAATCTTTTATTCGCTATTTTTCAAAGGCTTAAAGATCAAGGGAATACCCTCATT       720

CGTTTTGAACCGCAAGATTAAAAACGCATGATCATGGTCAAATCCAACTTAACCAACAGG       780

CAATTATTGCAAGTCTTAAAAAATTTGCTTGACAACATTAGCGGTGCTAATTTTTGGATC       840

AATTAGAGAGCATGTTGAAAATGGCGAAATCTATGAAGATCACACTAGCTACATGCTTTT       900

CAAACAATTTGAAATCCGCATCCATAAGCCAACACAAACTATAGAATACTTAGATGTCCA       960

ACTCAATGATAGCTATCAATACTTGCTCAACAATCTAGGAATGGGCGGTCAATACACTTC      1020

TTTCAATCTCTTAGAATTTCAAAGGGTGAGGGGCAAATAGTGAGAGCGTTAAATTTCCCC      1080

CCCCTATTCCCCTTAAAAAGGACCCTTATCCCAGGGAATTTTTGGCCCCAATACAATTAG      1140

GGCCAAAAACCCGGTCCCTTCCATGGCTTAACCAACCCAATTGGGGGATTCCAATTTCCC      1200

CTGGATGGGAATAACCCAAGGCTTTTTTTGAAAATTCCACCTACCATTTGGTCCAAAATT      1260

GGATGGACAATTCCAAATTCCAAATCTTCTTTTCCAAGAATGGGGGCCAACCCTTGACAA      1320

ACTCCTTAAACCTTTTCATTCGGCTAAAAGGTTGAAAAACATTTGGAAGATTTGGTTTAA      1380

GGAAATATTTATCGGGTGAAAAGACCAGATGCATGGCTAACTTAAACTCCATAGAAAAAC      1440

TGAATCACGAAAGAAAGAATGCTATCAAAAATGGCATTTACCACTTGATCCAAATCAAAT      1500

TTTCTTACAACTCCAATCGCATTGAAGGAAGCGGTTTGACTTATGAACAAACCGCTCATA      1560

TTTTTGACAAATCCGTTCTCATAACTGAAAAAAACACCAATATCAAACTTGATGATATTT      1620

TTGAAACTATCAATCATTTTGAATGCGTGAATTACTTGCTTGAAAGCTATAAAGAACCTT      1680

TGAGTTTAGAATACTTTAAGAATTTACACAAAATCTTGAAAAAGAATTGTTCTGATGAAG      1740

TTATTGGTGATTTTAAAAAACGCCCTAATTTTGTAGGCAATAGCGCCACAACAAGACCCA      1800
```

-continued

AATTAGTTGAAAGCGAATTGACAAATCTTGTGAAAAATTATCAACGCAACCTTGAAGTGA 1860

GTTTGAAAAACAATATCATGCCTTTCATCATAGAAAACGAACACAAAGCCTTTTACTACA 1920

GGGGCATCAAAGAATATGACAACACAAAAGGCTACTTGAAAGACACCATTTTGCAAAGTC 1980

AAGACAATTTCAATGAAATGGTTAGCTATTTCTTTTCTTGAGTGAAACCGCTTATTTTTG 2040

CTTGTGTGCTTTTGTTTTTTGCGTTTTTAGTTGTAGGTGGTAAGAAATATCGGTTTTTTG 2100

CTTTTCGTTGGTTGTAGGCGATTTTAGATAGCAAAAAACAGCTAAAAAATCCAAGCAACC 2160

TAATTGATTTCAAACCAACTTCATTTCCCTTTTAGTCGTTAGCCATTTAGCCAATCTAAC 2220

TAGTTTAGCATCTAAAAGCGCATATAACTTGAGTTAGCAATCCAACCAATACTAAAACCG 2280

CCTAGCGAAGCGTTAGCGAGCAAAATAAGCGGTTTTAGACCGATTGTTTGCTGACAAGCA 2340

AACACCAATAAGCGAGCGTTAGCGAGCATGGACAAAAGCGCATCGCAGTTTGAAAGCGTA 2400

GGCGTTAGCCGAAGCTGTTTTGCGTAAGCAAATCAAACAAGATAGCGCAAGCCGAGGTGC 2460

AGCCCAAGAATTTGAATTAATCCATGCGGTGTTTAGGGCGTTTTAGCGTGATCGCTTTAT 2520

TACATGTTTTAAACAGCATGCTGTTTTTTACATGTTTTACTCGCATGCGCGCGCGCTAGG 2580

TATTGGTGGTTGGAATAGCCTAAATAACGCAGCTGTATGGTTTCTCATTTTTCGGTGACA 2640

ATGAATAAGGGGTAGTTCTTGCGAGTCATAAGTGTAGTTCTTGCGAGTCATAAGTGTAGT 2700

TCTTGCGAGTCATAAGTGTAGTTCTTGCGAGTCATAAGTGTAGTTCTCTTCACAATATCT 2760

ACACAATTCACAATCTCTAGCTACAATAACAGCGTGTGAAGATGCTTTCACAGCGGTATT 2820

TCCTATGTGCGGCAAAATTTGGAGCAATTAGCTTTAAAAGCTAGTGGGTTGGGAGTTTGT 2880

AGCGGGTATGCACTCCGTTAGGAGGCACACCATGAAAGCATTTTTGATAGTAGTGATTTT 2940

AGTGGTAATCTTGACACAGCCACTATATTAAAACCTTAGCGTTTTAATAACCCTTATAAG 3000

TCCGCCAAGACTTCTTAAGGGTTTCACTCCTGTTATTATATCGTCTTTTGAAAAATAAGC 3060

ATTAAAAGGCGCTTAAATGCCCATGAATACGAATTTTGAACAGCTTAGAAAACAAGAATT 3120

GGAATTACGAAAATTATTAGAAGAATTAGAAACGCTCCCACAAACCCCACAAATTAAACT 3180

GCAAAAACAAAAAATACAAACTTACATAGACAAGATAACACCAAGTATTTTGAGCGGTTT 3240

TGATCAAAAATTCAAAGAAATTATAGAAAATCTATCAAATGAATTTGAAAAAGAAAAATC 3300

CACACCACTCAAAGAGCCACAAACCACCCCCACACCATGCAAAGATTTAGTGGTTAGCAC 3360

CCCTAAAGATAACACCTATACCACCTACCACAATAACGCTAATAAGGTCAATCTAGGGAA 3420

ATTGAGCGAAAGGGAAGCCAATCT 3444

An additional nucleotide sequence that was cloned is provided at SEQ ID NO: 4, which includes a 135 bp segment that encodes a peptide of 45 amino acids (SEQ ID NO: 5). This smaller 45 amino acid peptide is an immunogenic polypeptide of the Hepatitis C virus (HCV) core antigen. The nucleic acid sequence encoding the 45 amino acid peptide is shown below with the indicated 135 nucleotides underscored. (SEQ ID NO: 5)

SEQ ID NO:4

CATGAGCACG AATCCTAAAC CTCAAAGAAA AACCAAACGT AACACCAACC GTCGCCCACA GGACGTCAAG
TTCCCGGGTG GCGGTCAGAT CGTTGGTGGA GTTTACTTGT TGCCGCGCAG GGGCCCTAGA TTGGGTGTGC
GCGCGACGAG GAAGACTTCC GAGCGGTCGC AACCTCGAGG TAGACGTCAG CCTATCCCCA AGGCACGTCG
GCCCGAGGGC AGGACCTGGG CTCAGCCCGG GTACCCTTGG CCCCTCTATG GCAATGAGGG TTGCGGGTGG
GCGGGATGGC TCCTGTCTCC CCGTGGCTCT CGGCCTAGCT GGGGCCCCAC AGACCCCCGG CGTAGGTCGC
GCAATTTGGG TAAGGTCATC GATCGGGTTA CGTGCGGCTT CGCCGACCTC ATGGGGTACA TACCGCTCGT
CGGCGCCCCT CTTGGAGGCG CTGCCAGGGC CCTGGCGCAT GGCGTCCGGG TTCTGGAAGA CGGCGTGAAC
TATGCAACAG GGAACCTTCC TGGTTGCTCT TTCTCTATCT TCCTTCTGGC CCTGCTCTCT TGCCTGACTG
TGCCCGCTTC AGCCTACCAA

SEQ ID NO:5

AATCCTAAAC CTCAAAGAAA AACCAAACGT AACACCAACC GTCGCCCACA GGACGTCAAG TTCCCGGGTG
GCGGTCAGAT CGTTGGTGGA GTTTACTTGT TGCCGCGCAG GGGCCCTAGA TTGGGTGTGC GCGCG

Figure 3:
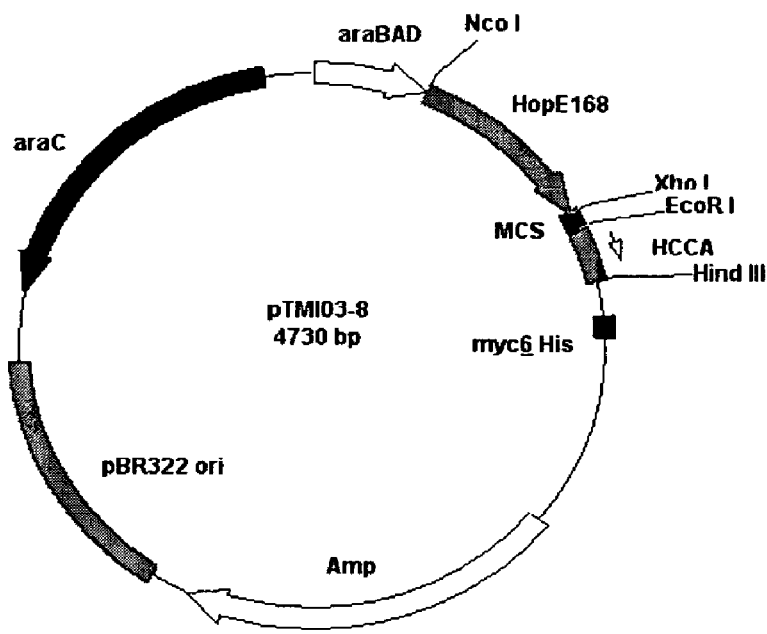
FIG. 3 in accordance with one embodiment of the invention, illustrates the vector construct, pTM103-8 (6× His tag disclosed as SEQ ID NO: 10).

The nucleic acid of SEQ ID NO: 4 was cloned into the hopE gene (SEQ ID NO: 6, shown below), of *H. pylori* 26695 at nt504 of SEQ ID NO: 4 (noted in bold/underscore; corresponding to amino acid residue 168 of the protein product) so that the expressed product would be located as part of the surface exposed loop of the HopE gene product. This construct, designated as vector pTMI03-8 (FIG. 3) was expressed on the surface of *E. coli*.

```
                                                        SEQ ID NO: 6
    ATGCCATAGC ATTTTTATCC ATAAGATTAG CGGATCCTAC CTGACGCTTT

TTATCGCAAC TCTCTACTGT TTCTCCATAC CCGTTTTTTG GGCTAACAGG

AGGAATTAAC C

1 ATGGAATTTA TGAAAAAGTT TGTAGCTTTA GGGCTTCTAT CCGCAGTTTT

51 AAGCTCTTCG TTGTTAGCCG AAGGTGATGG TGTTTATATA GGGACTAATT

101 ATCAGCTTGG ACAAGCCCGT TTGAATAGTA ATATTTATAA TACAGGGGAT

151 TGCACAGGGA GTGTTGTAGG TTGCCCCCCA GGTCTTACCG CTAATAAGCA

201 TAATCCAGGA GGCACCAATA TCAATTGGCA TGCTAAATAC GCTAATGGGG

251 CTTTGAATGG TCTTGGGTTG AATGTGGGTT ATAAGAAGTT CTTCCAGTTC

301 AAGTCTTTTG ATATGACAAG CAAGTGGTTT GGTTTTAGAG TGTATGGGCT

351 TTTTGATTAT GGGCATGCCA CTTTAGGCAA GCAAGTTTAT GCACCTAATA

401 AAATCCAGTT GGATATGGTC TCTTGGGGTG TGGGGAGCGA TTTGTTAGCT

451 GATATTATTG ATAACGATAA CGCTTCTTTT GGTATTTTTG GTGGGGTCGC

501 TATCGGCGGT AACACTTGGA AAAGCTCAGC GGCAAACTAT TGGAAAGAGC

551 AAATCATTGA AGCTAAGGGT CCTGATGTTT GTACCCCTAC TTATTGTAAC

601 CCTAACGCTC CTTATAGCAC CAAAACTTCA ACCGTCGCTT TTCAGGTATG

651 GTTGAATTTT GGGGTGAGAG CCAATATTTA CAAGCATAAT GGCGTAGAGT

701 TTGGCGTGAG AGTGCCGCTA CTCATCAACA AGTTTTTGAG TGCGGGTCCT

751 AACGCTACTA ATCTTTATTA CCATTTGAAA CGGGATTATT CGCTTTATTT

801 AGGGTATAAC TACACTTTTT

CTCGAGATCT GCAGCTGGTA CGATATGGGA ATTCGAAGCT TTCTAGAACA

AAAACTCATC TCAGAAGAGG ATCTGAATAG CGCCGTCGAC CATCATCATC

ATCATTGAGT TTAACGGTCT CCAGCTTGGC TGTTTTGGCG GATGAGAGAA

GATTTTCAGC CTGATACAGA TTAAATC
```

Briefly, one method of accomplishing the isolation of hopE gene is amplification from *H. pylori* 22695 by using Taq DNA polymerase. The upstream primer 5'-AAGGATCCGATAGGAATGTAAAGGAATGG-3' (SEQ ID NO: 7) containing a BamHI site and the downstream primer 5'-CCGAATTCTAAAGGCATGAACGCTTGCA-3' (SEQ ID NO: 8) containing an EcoRI site can be constructed by using a DNA synthesizer, such as the Perkin-Elmer Applied Biosystems, Inc. model 332 (ABI; Mississauga, Ontario, Canada). The resulting PCR fragment can be blunt-end cloned into the EcoRV site in pBluescript II KS(+) in the same orientation as the lac promoter.

PCR primers can then be designed to insert two unique restriction enzyme sites into the hopE gene for insertion of the 135 bp immunogenic coding sequence from the Hepatitis C virus (HCV) core antigen. The PCR amplification using Taq DNA polymerase can be performed using a touchdown amplification procedure as follows. The PCR Thermocycler is programmed for an initial denaturation step of 96° C. for 4 min, followed by 18 cycles at an initial annealing temperature of 65° C. (for 90 s), which is decreased by 0.5° C. for each successive cycle, an extension step at 72° C. for 6 min., and denaturation at 96° C. for 1 min. Subsequent to completion of the first 18 cycles, an additional 14 amplification cycles can be performed by using 72° C. extension and 96° C. denaturation steps with a constant 55° C. annealing temperature. The resulting amplicon is then purified by column, precipitated with ethanol, and made blunt by digestion with the Klenow fragment of DNA polymerase. The PCR products can be digested with restriction enzyme to remove the template DNA, and religated into an appropriate vector such as pTMI03.8 under the control of the arabinose inducible promoter, and transformed into *E. coli* JM105.

Recombinant clones can be identified by using oligonucleotide primer 5'-AGATCTAAGGACGTC-3' (SEQ ID NO: 9) plus the reverse sequencing primer in PCR amplification reactions. Identified clones can be sequenced to verify that the inserted restriction endonuclease sites are in frame and that no errors had been introduced into the hopE gene. The 135 bp immunogenic coding sequence from the Hepatitis C virus (HCV) core antigen can then be inserted using standard techniques.

Once vector pTMI03-8 had been created, it was transformed into *E. coli*, which was grown at 37° C., cells were then harvested and the expression of the DCV insert was continued by Western Blot.

Briefly, a procedure for this is as follows. Cells are harvested from about 20 plates and resuspended in 20% sucrose with 50 mg of DNase I (Boehringer Mannheim) in 10 mM Tris-HCl (pH 8.0). The cells are then disrupted with a French press at 15,000 lb/in$^2$. Broken cells are overlaid on a sucrose step gradient of 1 ml of 70% and 6 ml of 70% sucrose in 10 mM Tris-HCl (pH 8.0). The outer membrane fraction is collected and pelleted at 150,000×g, and the pellet is resuspended in 100 ml of distilled water.

Alternatively, outer membranes from 500 ml of log-phase culture can be solubilized in 10 mM Tris-HCl (pH 8.0)-3% n-octyl-polyoxyethylene incubated at 23° C. for 1 hour and centrifuged for 30 mm at 173,000×g. The pellet is resuspended in 10 mM Tris-HCl—3% n-octyl-polyoxyethylene-5 mM EDTA (pH 8.0), incubated at 23° C. for 1 hour, and centrifuged for 30 min at 173,000×g, and the supernatant collected. A Western immunoblot indicated the presence of HCV/hopE in the supernatant of the second solubilization step. The supernatant containing HCV/hopE is mixed with an equal volume of 0.125 M Tris-HCl (pH 6.8), 4% (wt/vol) sodium dodecyl sulfate (SDS), and 20% (vol/vol) glycerol and subjected to SDS-12% polyacrylamide gel electrophoresis (PAGE). If required the HCV/hopE band can be excised from an unstained portion of the gel and eluted overnight at 4° C. into 10 mM Tris-HCl (pH 8.0), 1 mM EDTA (pH 8.0), and 100 mM NaCl. The elution supernatant can then be run on an SDS-PAGE gel to check for purity and a Western immunoblot using standard techniques undertaken. For example, isolated outer membranes can be loaded at a concentration of 15 μg/lane. Electrophoresis is then carried out by SDS-PAGE on a discontinuous 12% polyacrylamide gel. Proteins are then stained with Coomassie brilliant blue. For Western immunoblotting, unstained gels can be electroblotted onto immobilon-P membranes (Millipore, Bedford, Mass.). After blocking for 2 h at 2° C. with 3% bovine serum albumin (BSA; Boehringer Mannheim)—0.1% Tween 20 (Sigma) in phosphate-buffered saline (PBS), the membranes are then incubated with a 1/10,000 dilution of anti-HCV rabbit antiserum in 1% BSA-0.05% Tween 20 in PBS for 1 h at 37° C. The membranes are then washed with PBS and incubated with a 1/5,000 dilution of an alkaline phosphatase-conjugated secondary antibody (Bio-Rad, Richmond, Calif.) for 1 h at 37° C. The bound antibodies are detected with 5-bromo-4-chloro-3-indolylphosphate (BCIP, Calbiochem. La Jolla, Calif.) and nitroblue tetrazolium (NBT, Sigma).

Example 2

Expression Vectors and Selection of Antigens for Stable Expression

Because HopE is a native protein of *H. pylori*, it is tolerated by this organism and can thus form a construct useful for expressing foreign antigens or other heterologous gene products in *H. pylori*. Other *H. pylori*, *E. coli* shuttle vectors that can be readily developed as described above include, for example, vectors comprising two plasmid ori sites and markers which are suitable for each host. Markers might include genes for chloramphenicol/kanamycin resistance as well as promoters that can be recognized by both the *E. coli* and *H. pylori* transcriptional systems.

The requirements for replication *E. coli* can be achieved by using any of a number of known *E. coli* plasmids (e.g., pBR322).

Constructed shuttle vectors can be tested for replication in both *E. coli* and *H. pylori* in vitro and compared to existing shuttle plasmids described in the literature.

The choice of antigen or other heterologous gene product to be expressed would ideally be one that is not toxic to *H. pylori* and *E. coli* and that is highly immunogenic (or possesses another desirable property) when delivered to a selected site in a mammal. In the case of an expressed antigen for immunization of the mammal, such as site may be a mucosal site.

As described in Example 1, hopE/HCV core antigen fusion protein can be expressed at the *E. coli* surface. The product of pTMI03-S (FIG. 3) is preferably targeted to the *H. pylori* outer membrane, so that it would display the HCV core antigen in a mucosal environment.

Tetanus toxoid (TT) has been studied extensively as an antigen in humans, and immune responses to it are well characterized. TT elicits good mucosal immune responses when administered orally or intranasal when displayed on the surface of bacterial spores (Duc & Cutting, 2003, *Expert Opinion Biol Ther*, 3(8), 1263-70). The tetanus toxin C fragment can be fused to the hopE gene product as described above or engineered to contain a membrane anchor and cell surface target sequence. The advantage of this system is the existence of well-characterized murine models for assessment of the effectiveness of the vaccination procedure, whereas; in the case of HCV where the known murine models typically rely on immune-deficient mice. The gB protein of cytomegalovirus (CMV) has been shown to immunize mice against a lethal dose of an engineered vaccine virus expressing the gB antigen. Accordingly, shuttle vectors such as those described herein, comprising gB antigen in place of an HCV antigen can be constructed using the protocol described in Example 1.

A number of promoters can be used in the shuttle vectors. Ideally the promoter used is inducible either by a natural in vivo colonization mechanism of *Helicobacter* or by induction with an innocuous foodstuff or chemical that can be consumed. For example, the promoter from the *H. pylori* histidine kinase HP 165 may be used. The promoter from the *H. pylori* histidine kinase HP 165 is reported to be induced by acidic pH and may be a virulence factor related to gastric mucosa colonization. The benefit of this promoter is that a construct can be made in vitro. The foreign antigen will only be expressed when exposed to the acidic environment of the gastric mucosa.

Other promoters include the arabinose inducible promoter used in pTMI03.S and FlaB sigma 54 promoters (Josenhans et al., 1998, *EEMS Microbial Lett.*, 16 1(2), 263-73), the T7 promoter used in constitutive and inducible *E. coli* systems and the nir promoter of *Salmonella* which is induced in anaerobic environments (Chatfield et al., 1992, *Biotechnology*, 10(8): 888-92). The ability of any of these promoters to function in *H. pylori* can be tested using the system developed by Angelini et al. (2004) (*Plasmid*, 51:101-107) that uses CAT and GFP reporters as readout of promoter activity in a *H. pylori* plasmid vector.

The target sites of expression will depend on the antigen or other gene product used. Initial studies focused on HopE proteins and fusion polypeptides which target the expressed polypeptide (e.g., antigen) to the cell surface of *H. pylori*.

Plasmid stability is also very important and, while the use of antibiotic resistance genes as selective determinants for plasmid maintenance is useful in vitro, is less practical in vivo. An alternative is a balanced-lethal system, for example, the asd gene that is used inactivated in *Salmonella*. The asd gene, which exists natively in *H. pylori*, encodes aspartate-β-semialdehyde dehydrogenase (an enzyme in biosynthetic pathway for diaminopimelic acid (DAP), an essential component of the cell wall peptidoglycan of gram-negative bacteria. In the absence of DAP, asd mutants undergo lysis. Since DAP is not present in mammalian tissues, this balanced-lethal system imposes a requirement that all living *H. pylori* carry the recombinant asd gene-containing plasmid.

In order use the asd gene system the genomic copy of the asd gene is inactivated using standard gene knockout protocols. This strain of *H. pylori* will then only grow with the supply of DAP or with a plasmid that contains the asd gene.

Other systems that can be used for similar purposes include *E. coli* enterotoxin or cholera toxin (CT) as mucosal adjuvants. Adjuvants can also be used to boost the mucosal immune response. Two such adjuvants are CT and *E. coli* enterotoxin (LT) wherein expressed antigens are fused to the LTB and CTB mutants that maintain their strong mucosal adjuvant properties but have reduced toxicity.

Example 3

Virulence, $LD_{50}$

As described in Examples 1 and 2, *Helicobacter*-based vectors such as pHP3 and pHP623 are capable of providing protection against infection in a mammal, such as a mouse or human. In the present example, a murine model is used to demonstrate the utility of using the *Helicobacter*-based systems to provide delivery of a pharmacologically active molecule of interest to a mammal, including a human. The murine model is employed to demonstrate the activity of a transgenic strain of *H. pylori* to elicit a serological response to an expressed surface antigen in vivo.

Mice are infected with wild-type *H. pylori*, while other mice are inoculated by gavage with temperature-sensitive *H. pylori* as described in Example 2. Sera from both control and test animals are assayed for antibody and gastric histology are performed on sacrificed animals in accordance with the schedule shown in Table 1. A mouse urea breath test can also be used.

A 50% decrease in virulence (from 75% to 40%) was observed. Specific antibody titer increased 4 fold above baseline, indicating a serological response. Serum samples were taken at baseline, 12, 24 and 48 weeks. At these times 10, 10 and 20 animals were sacrificed and gastric histology performed.

Example 4

Comparison of Virulence and Antigenicity of Temperature Sensitive *H. Pylori* Strains In order detect change in virulence related to expression/modification of an outer membrane protein; mice were inoculated with temperature-sensitive *H. pylori* as described in Example 3. An equal size control group of mice were infected with a wild type *H. pylori* strain. Noninvasive means were used to determine presence or absence of *H. pylori*. Mice were bled at 3 and 6 months for antibody determination. At sacrifice, histology was performed to assay gastritis and confirm colonization.

Example 5

$LD_{50}$ Study to Evaluate Temperature-Sensitive *H. Pylori* Vaccine Efficacy for a Pneumococcal Antigen In order to demonstrate the *Helicobacter*-based vaccine protection effect from a standard pathogen (*pneumococcus*), mice were inoculated with temperature sensitive *H. pylori* by gavage. An equal sized control group was infected with the wild type *H. pylori* strain. Non-invasive means were used to determine presence or absence of *H. pylori* as described in Example 4. At 6 months post infection, all mice were given intraperitoneal challenge with 10 times the $LD_{50}$ of live virulent pneumococci type 4 (~20 CFU/mouse), as per the method of Aaberge et al. (1995, *Microb. Pathog.*, 18:141-152), Allowing for 75% lethality in the controls, the study has a power of 0.8 to detect a 50% decrease in mortality (75% vs 50%).

Example 6

Determination of *H. Pylori* Status of Mice

Breath Test Method

In the present example, the urea breath test used in humans was adapted for use in mice.

Ten mice were fed a diet devoid of urease (uncooked soy). Mice were then administered 3.7 kBq$^{[14]}$ C urea in 200 μl flavored citrate by gavage and placed in air-filled 2 L plastic Ziploc bags for 20 minutes. Mice were then removed without exchanging the air within the bag. Hyamine, 0.1 mmol in ethanol, was then introduced and scintillant was added to the hyamine solution and counted for 10 min or up to a count of 1,000 dpm.

Example 7

Human Studies

To confirm virulence and antibody response in humans, a strain of *H. pylori* like the "Baylor Strain" will be employed, and the following criteria will be adopted:

1. The infected individuals have no symptoms, no more than mild histological damage, and no evidence of infection with hepatitis viruses or HIV.

2. The isolate is a single strain, cagA negative, and sensitive to metronidazole, clarithromycin, tetracycline, and amoxicillin, 3. Volunteers to receive a challenge are healthy with normal gastric histology, no history of peptic ulcer, no young children at home, no regular contact with young children, and no allergies to the antibiotics that might be required to treat the infection.

Challenge will consist of 40 mg famotidine at bedtime followed by administration of *H. pylori* in beef broth orally in the morning. Subjects are contacted daily for 14 days. A 13c-UBT is performed after 7 and 14 days and endoscopy with quantitative culture and histology after 2 weeks and 3 months. Antibiotics are used to eradicate the infection.

Example 8

Figure 4:
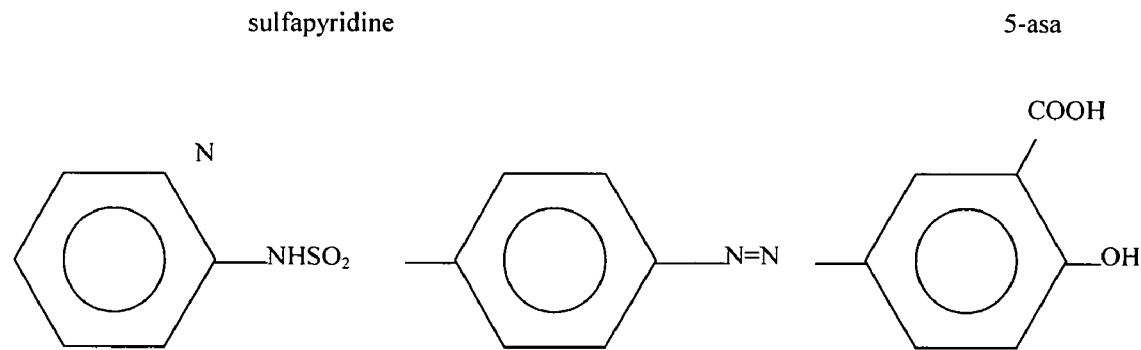
FIG. 4, in accordance with one embodiment of the invention, illustrates the chemical structure of sulfasalazine (SSN).

Development of External Chemical Marker for Detection of Wild Type and/or TSHP In Vivo An example of a chemical marker that may be used for the detection of wild type or TSHP in vivo is sulfasalazine (SSN), the structure of which is shown in FIG. 4. Studies in germ free mice and conventional rats have shown that intestinal bacteria are solely responsible for the diazo-bond reduction, resulting in the reductive catabolism of SSN and the release of sulfapyridine and 5-aminosalicylate. The enzyme(s) which catalyses this reaction is referred to as diazoreductase(s) (synonym azoreductase(s)). Conventional rats given SSN excrete 5-aminosalicylate and sulfapyridine (and their respective conjugates) in urine and feces, whereas germ-free rats show no evidence of SSN degradation.

Several bacterial species have been shown to have diazoreductases (AZR's). Preliminary bioinformatic studies have indicated that *H. pylori* may not contain the AZR gene. The presence of similar analogous sequences has also produced a negative result. Under these circumstances a transgenic strain of *H. pylori* (TSHP) that has a viable and functional azoreductase (azr+TSHP) can be used to assess the use of these markers.

Plasmid pTM103-02 is digested by EcoRI and HindIII, and ligated with the Azoreductase (AZR) gene from *Bacillus subtilis* treated with EcoRI and HindIII to generate a vector containing both HopE 168aa and AZR named pTMI03-azr. This plasmid is transformed into *E. coli* to assess whether expression of HopE and the *B. subtilis* AZR occurs. pTMI02 when similarly treated with full-length hepatitis C core antigen (HCCA) demonstrated transport of HopE::HCCA to *E. coli* outer membrane employing western blots and anti-HopE Abs.

Mice (n=30) are infected with the azr+TSHP by gavage and once AZR expression in vivo to produce 5-aminosalicylate and sulfapyridine (and their respective conjugates) in urine and feces is established, human trials can begin.

Example 9

Use of Diagnex Blue as a Marker

Figure 5:
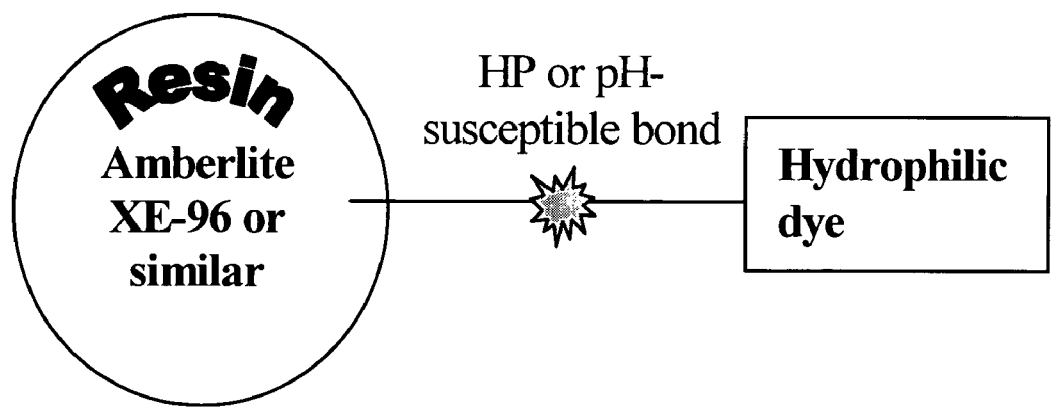
FIG. 5, in accordance with one embodiment of the invention, illustrates a schematic using an ion exchange resin (Amberlite XE-96) conjugated with a dye (Azure-A).

The diagnostic agent "diagnex blue" consists of an ion exchange resin (Amberlite XE-96) conjugated with a dye (Azure-A). This test relies on the fact that the resin-dye combination disassociates at pH less than 2.5 after which the dye is absorbed and appears in the urine. Persons without dye in the urine are achlorhydric. This principle is shown in FIG. 5.

The same principle can be used to test for *H. pylori*. For example, a dye-resin combination that disassociates at pH >7.0 could detect urease if the resin was given with urea. This would produce a pH >7.0 in the mucosal layer where *H. pylori* resides, thus releasing the dye.

Mice (n=30) are inoculated with a wild type *H. pylori* strain while germ-free mice (n=30) are used as controls (Pilot study). After an optimal period allowing for the *H. pylori* to establish an active infection, the test group and the controls are introduced with a predetermined quantity of the resin-dye complex by gavage. This will be followed by a urea solution. (Range 0.01M to 0.5M). The mice are kept in metabolic cages and the excretion of the azure dye are monitored and quantified. Different ratios of the resin and urea concentrations are tested to verify the optimal combinations to be used.

Example 10

Delivery Formulations

For administration by aerosol, the present invention can be delivered in the form of aerosol spray presentation from pressurized packs or a nebulizer, with the use of a suitable propellant. In the case of a pressurized aerosol, the dosage unit can be determined by providing a valve to deliver a metered amount. The formulation would be prepared as a powder for administration by inhalation. Administration by inhalation can also be carried out by atomizing solutions or suspensions which contain the compositions according to the invention.

The compositions according to the invention may also be formulated in a liquid for oral digestion for administration to a subject as an intravenous preparation.

All of the various preparations of the invention may be prepared by procedures familiar to those skilled in the art, if appropriate, using further suitable pharmaceutical auxiliaries. Compositions according to the invention advantageously contain the species of *Helicobacter*, alone or in combination with other desired ingredients.

Any of the above individual or combination of *Helicobacter* formulations may be included in a pharmaceutical composition comprising the pharmaceutically acceptable composition according to the present invention. The pharmaceutical compositions as described herein may be in solid (e.g. powder, particles, granules, sachets, tablets, capsules etc.), semi-solid (gels, pastes etc.) or liquid (solutions, dispersions, suspensions, emulsions, mixtures etc) form and adapted for administration via e.g. the gastrointestinal tract and gastric mucosa. The pharmaceutical compositions may thus be in powder or particulate form adapted to be dispersed in an aqueous medium before use.

A pharmaceutical composition in liquid form may be in the form of a dispersion comprising the *Helicobacter* composition and an electrolyte solution such as, e.g. a composition that is adapted to physiological conditions e.g. a physiologically acceptable solution.

A pharmaceutical composition according to the invention may further comprise another therapeutically, prophylactically and/or diagnostically active substance.

In another aspect, the invention relates to a pharmaceutical kit comprising a first and a second container, the first container comprising a recombinant *Helicobacter* composition comprising the plasmid and/or plasmid vector according to the invention and the second container comprising a dispersion medium for the *Helicobacter* composition, accompanied by instructions for administering and/or dosing the *Helicobacter* composition in the dispersion medium before use.

The *Helicobacter* composition according to the present invention contained in the kit may be in powder or particulate form.

A pharmaceutical kit according to the present invention may include instructions with recommendations for the time period during which the *Helicobacter* composition should be administered after dispersion in the dispersion medium.

Example 11

Immune Modulation with *Helicobacter*

Vaccine Preparation

The TH1 response (T-helper cell type 1) is a cell mediated response. Over activity of this is a presumed cause of diseases such as rheumatoid arthritis (RA) and Lupus. In contrast, TH-2 is an antibody type serological response characteristic of vaccines. The present example provides a technique to obtain a TH-2 type response in an animal when treated with a *Helicobacter*-based vaccine treatment preparation according to the present invention.

Use of the *Helicobacter* vectors and vector plasmid systems as described herein may be used to invoke antibody response in an animal. By way of example, a system employing a gene expression cassette in a construct that provided for the transformation of the bacterium, *Clostridium*, and the subsequent secretion of a protein (S-layer protein) from the surface of the transformed *Clostridium*, this resulting in initiation of mucosal vaccination, is described in WO-0194599, which disclosure is hereby incorporated herein in its entirety. These constructs may also include a secretory leader sequence selected from ORF1, ORF3, ORF5-7, ORF7 or ORF11.

In accordance with some embodiments of the vaccine, the *Helicobacter*-based vectors and vector plasmids may comprise a sequence encoding a bacterial surface layer protein. A surface layer protein is defined herein as any molecule of proteinaceous nature, including e.g., protein, glycol-protein or lipoprotein occurring in the outer membrane of a bacterium and capable of being exposed on the surface of the bacterium. S-layer proteins may be continuously and spontaneously produced in larger amounts than any other class of protein in the cell.

A process for preparation of a recombinant cell preparation comprising a gram negative host cell, *Clostridium*, having the S-layer protein, is also provided in WO-97/28263. The process may be modified and followed in accord with the procedures described herein to incorporate an S-protein as part of the *Helicobacter* constructs of the present invention.

Accordingly, in some of the vector and vector plasmid constructs, a fusion protein is provided that comprises a *Helicobacter* sequence and a non-*Helicobacter* pharmacologically active molecule of interest. In order to enhance the immunogenicity of a vaccine employing the *Helicobacter* constructs of the present invention, the *Helicobacter* sequence of the fusion protein may comprise a sequence encoding an S-layer protein. *Bacillus* constructs that include the S-layer protein as part of a fusion protein have been reported to express the S-layer protein at the *Bacillus* surface. (See WO-95/19371, describing *Bacillus sphaericus*), thus enhancing the immunogenicity of the preparation.

Mucosal immunization is already provided against some diseases, including an oral polio vaccine and an oral (drinkable) vaccine against cholera and diarrhea due to *E. coli* (an inactivated vaccine). In some embodiments, it is contemplated that the vaccines of the invention may thus comprise an inactivated vaccine.

The present invention contemplates a live vaccine, as such will provide a single-dose, long lasting vaccination, because the carrier organism, *Helicobacter*, will continue to produce the antigen, i.e., non-*Helicobacter* pharmacologically active molecule of interest, and boost immunity in vivo. In addition, the vaccines will be administered in combination with an adjuvant. These adjuvants' comprise molecules such as aluminum hydroxide or lipid vesicles that increase the exposure time for the vaccine by slowing its removal forte site of administration. Adjuvants' also act by evoking production of immunomodulatory peptides called cytokines and chemokines (Brewer et al. 1997, *J. Cytokines Cell Mol. Ther.*, 4:223-246). Thus, the present vaccines may comprise cytokine adjuvant to enhance immune response.

The transformed *Helicobacter* or *E. coli* bacterium, when administered orally or gastrically to a mammal such as a human or animal, will provide for the gastro-intestinal colonization, production and presentation of the desired polypeptide, through the gastric wall, which is the natural site of colonization. The gastro-intestinal tract is surrounded by an immense immune apparatus specialized in mounting immune response of various types. Gastro-intestinal colonization by recombinant *Helicobacter* vaccine or peptide producer strain thus enables a much longer immune stimulus than traditional vaccination. Additionally, antigen can be presented preferentially to the gut wall or the lumen.

Example 12

*Helicobacter* and Uses Thereof as an Appetite Suppressant

The present example is provided to demonstrate the utility of the present invention as a method for employing *Helicobacter* in preparations and treatment regimens that provide for appetite suppression. In particular, delivery to the gut mucosa of a construct that comprises attenuated *Helicobacter* together with a non-*Helicobacter* pharmacologically active molecule of interest that regulates the level of ghrelin or an agonist of ghrelin, is expected to provide an effective means for providing suppression of the gut-brain axis that regulates appetite and sanity.

Studies have suggested that ghrelin is an appetite stimulant, i.e., ghrelin increases food intake in mice (Asakawa et al. 2003, *Gut*, 52(7):947-52). Ghrelin has also been reported to reduce fat utilization in adipose tissue in rodents (Tschop et al., 2000, *Nature*, 407: 708-13), as well as to be involved in rat adipogenesis (Choi et al. (2003), *Endocrinology*, 144 (3): 751-9). Ghrelin has also been reported to be a hunger signal, prompting the subject to eat when nutrition availability is low.

Ghrelin, an endogenous ligand for the growth hormone secretagogue receptor (GHS-R), stimulates growth hormone (GH) release from cultured pituitary cells in a dose-dependent manner, and is produced and secreted from the A-like cells found mainly in the oxyntic glands of the gastric fundus. Ghrelin is now known to play a role in not only GH release, but also in controlling the appetite and body weight.

Both parenterally and intracerebro-ventricularly administered ghrelin have been shown to stimulate food intake and increase the body weight of mice and rats with free access to food, even those animals with GH deficiency. The control of appetite and body weight may be independent of GH release.

Ghrelin, a 28-amino-acid peptide, is activated when its third serine residue is acylated by n-octanoic acid, and GHS-R is responsive to the first four or five residues including the octanylated serine residue of the whole ghrelin peptide. GHS-R has been shown to be present in the pituitary, hypothalamus, adrenal glands, thyroid, pancreas, myocardium, spleen and testes. Ghrelin stimulates the expression of both NPY and AGRP mRNA in the hypothalamus. The central orexigenic effect of ghrelin is mediated by the NPY/AGRP-expressing neurons in the hypothalamus. Ghrelin has also been reported to suppress vagal afferent activity. The peripheral orexigenic effect of ghrelin may be mediated, at least in part, by its suppressive effect on the vagal afferent activity. IL-1β is a pro-inflammatory cytokine that mediates the cachectic process by stimulating the expression and release of leptin, and/or by mimicking the effect on the hypothalamus of excessive negative-feedback signaling from leptin.

It is proposed that antagonists to ghrelin if provided to the animal at the gut mucosa will reduce food intake by an animal and reduce body weight gain.

Example 13

Cell Wasting Attendant Cancer and AIDS

The present example demonstrates the utility of the present invention for use as a preparation that will prevent or inhibit cell wasting, particularly cell wasting associated with diseased states of AIDS and cancer.

Cachexia is a condition characterized by wasting, emaciation, feebleness and inanition. It was recently reported that the levels of both ghrelin peptide and ghrelin mRNA in the stomach were up-regulated in a mouse model of cancer cachexia. In cachectic mice with increased plasma levels of IL-1β, the plasma concentrations of ghrelin also increased with the progression of cachexia. This result suggests that a close relationship might exist between the ghrelin dynamics and the cachectic process mediated by IL-1. IL-1β is an anorexigenic substance, just like CCK, leptin, gastrin-related protein and bombesin, and antagonizes the actions of ghrelin.

Asakawa et al. reported that parenterally administered IL-1β decreased NPY mRNA expression in the hypothalamus and preproghrelin mRNA expression in the stomach, and that intraperitoneally administered ghrelin inhibited the severity of IL-1β-induced anorexia. *Helicobacter pylori* infection is known to be a major pathogenetic factor in the development of gastritis, peptic ulcer disease and gastric malignancy. Attachment of *H. pylori* to the gastric mucosa induces inflammation, which is associated with the release of various cytokines, including IL-1β.

It has been observed clinically that *H. pylori* eradication is often followed by improvement of some nutritional parameters, such as the body weight and the serum levels of total cholesterol, total protein and albumin. *H. pylori* infection has been reported to be capable of modifying the plasma and gastric ghrelin dynamics in Mongolian gerbils. In humans, however, *H. pylori* infection has been reported not to be associated with any changes of the plasma ghrelin levels, although eradication of *H. pylori* has been shown by some to be associated with increases of the plasma ghrelin levels.

It is proposed that *H. pylori* may be used as a carrier to provide amylin to a patient in need thereof, by, for example, acting as a carrier vehicle, to the gastric mucosa. In some embodiments, the *Helicobacter* carrier will be constructed so as to include amylin, amylin agonist, analogs, and derivatives, and amylin agonists (including calcitonins, calcitonin gene-related peptides), and analogs therefore to decrease ghrelin levels.

Amylin antagonists can increase ghrelin levels. Modulation of the effective levels of amylin, with amylin, amylin agonists, amylin antagonists, or other compounds that decrease the effective level of amylin such as antibodies, may inhibit, or stimulate in the case of antagonists and antibodies, ghrelin secretion. Hence, some embodiments of the method are directed to modulating endogenous levels of ghrelin by increasing the effective level of amylin or amylin agonists in the body, by direct or indirect means, or by decreasing the effective level of amylin using amylin antagonists or inhibiting amylin production.

Example 14

Treatment of Gauchers Disease

The present example demonstrates the utility of the invention for use as a treatment for a disease resulting from an enzyme deficiency, such as Gaucher's disease. Gaucher's disease is the most common lysosomal storage disorder in humans, and results from a deficiency of the enzyme, glucocerebrosidae (GC). (Nolta et al., (1992), *J. Clin. Invest.* 90 (2):342-348).

Enzyme replacement therapy is provided with a *Helicobacter* vaccine construct that comprises a sequence encoding chemical chaperones. (Sawker et al., (2002), *PNAS* USA 99(24): 15428-15433). An enhanced level of functional β-glycosidase (β-Glu, glucocerebrosidase) may thus be obtained. In particular, the chemical chaperone deoxynojirimycin (NN-DNJ) is to be used in the *H. pylori* construct and administered to the patient orally or intragastrically.

As part of yet another embodiment of the methods, a *Helicobacter*-based construct as described herein comprising a vector having a non-*Helicobacter* pharmacologically active molecule of interest, in this case, encoding glucocerebrosidase (GC). Retroviral mediated transfer of glucocerebrosidase cultured Gaucher bone marrow is described as one approach for treating Gauchers disease in Nolta et al. (1992). However, this approach is extremely invasive. Alternative enzyme replacement therapy employing the *Helicobacter*-based constructs of the invention that include a sequence encoding for the deficient enzyme, glucocerebrosidase, provides a much more attractive and less expensive alternative to such a therapy.

Example 15

The present example is presented to demonstrate the utility of the present invention to provide a useful preparation that is suitable for treating and/or inhibiting a bacterial induced malignancy, such as lymphoma, particularly MALT lymphoma, using a vaccination preparation comprising the *Helicobacter* vector and/or plasmid vectors as described herein.

Sutton et al. (2004) (*Vaccine,* 22 (20): 2541-6) report protection against a bacteria-induced malignancy, specifically primary gastric MALT lymphoma, as a result of vaccination/immunization of an animal against *Helicobacter felis*.

Therefore, the *Helicobacter pylori* constructs of the present disclosure that include a vector and/or plasmid vector suitable for providing an immunizing preparation that includes an immunogene antigen of interest other than *Helicobacter felis*, may also be used to provide vaccination protection against a bacterial-induced malignancy, and in particular, against primary gastric MALT lymphoma. By way of example, some embodiments of the plasmid vector would include a fusion protein comprising a *Helicobacter pylori* encoding sequence and a non-*Helicobacter pylori* encoding sequence that is, for example, other than a *Helicobacter felis* antigen species.

All documents, patents, journal articles and other materials cited in the present application are hereby incorporated by reference.

Although the present invention has been fully described in conjunction with several embodiments thereof with reference to the accompanying drawings, it is to be understood that various changes and modifications may be apparent to those skilled in the art. Such changes and modifications are to be understood as included within the scope of the present invention as defined by the appended claims, unless they depart therefrom.

BIBLIOGRAPHY

The following references are specifically incorporated herein by reference.
1. U.S. Pat. No. 6,570,004—Blaser et al (2003).
2. U.S. Pat. No. 6,680,179 Collins et al.
3. U.S. Pat. No. 6,383,496—Curtiss et al (2002).
4. U.S. Pat. No. 6,150,170—Powell et al. (2000).
5. U.S. Pat. No. 6,410,012—Seizmore et al. (2002).
6. U.S. Pat. No. 6,550,419—Hone et al. (2002).
7. U.S. Pat. No. 6,531,313—Goudsmit et al. (2003).
8. U.S. Pat. No. 6,682,729—Powell et al (2004).
9. U.S. Patent Publication 2005/0075298A1—Chen et al. (2005).

10. U.S. Patent Publication 2002/0176848A1—Seizemore et al. (2002).
11. U.S. Patent Publication 2005/0096288 A1—Guevara et al. (2005).
12. U.S. Patent Publication 2004/0236072 A1—Olmsted et al. (2004).
13. U.S. Patent Publication 2004/0203039 A1—Hensel et al. (2004).
14. U.S. Patent Publication 2004/0005325 A1—Kusters et al. (2004).
15. U.S. Patent Publication 2002/0032152 A1—Torossian (2002).
16. U.S. Patent Publication 2003/0170264 A1—Turner et al. (2003).
17. U.S. Patent Publication 2003/0204068—Blasec et al. (2003).
18. U.S. Patent Publication 2002/0161192 A1—Meyer et al. (2002).
19. WO 96/33274—Covacci et al. (1996).
20. WO 99/21959—Ellis et al. (1999).
21. WO 01/94599—Burman et al. (2001).
22. WO 2005 021026—Baron, et al. (2005).
23. Graham et al (2002), Gastroenterology, 123:1637-1648.
24. Liu et al (2005), World Journal Gastroenterology, 11(14): 2154-2156.
25. Conway, B R (2005), *Curr. Pharm. Res.,* 11(6) 775-90.
26. Sawker et al (2002), PNAS USA, 99(24): 15428-15433.
27. Sutton, P et al (2004), Vaccine, 22(20): 2541-6.
28. Kang et al (2005), World Journal Gastroenterology, 11(3): 454-456.
29. Moschos et al (2004), Immunology and Cell Biology, 82(6): 628-637.
30. Reddy et al (2004), International Journal Antimicrob. Agents, 24(6): 536-47.
31. Bai et al. (2003), Sheng Wugong Cheng Xu Bao, 19(4): 433-8.
32. Nolta et al. (1992), Journal of Clin. Invest, 90(2): 342-348.
33. Shi et al. (2005), *Helicobacter,* 10(1): 71-9.
34. Deml et al. (2005), Infection Immunity, 73(8): 4732-42.
35. Cosima et al. (2005), Trends in Immunology, 26(4): 199-207.
36. Velin et al. (2005), Gastroenterology, 129(1): 142-155.
37. Kong et al. (2000), Nucleic Acids Research, 28(17) 3216-3223.
38. Mao et al. (2003), World Journal of Gastroenterology, 9(7): 1529-1536.
39. Chu et al. (2005), World Journal of Gastroenterology, 11(23): 3518-22.
40. Kathy Parton. (2000), Institute of Veterinary, Animal and Biomedical Sciences, "*Helicobacter mustelae* as vector for biological control in stoats" Wildlife Health and Conservation Research Program; Landcare Research (Funding Body).
41. Forrester N. T., Parton, K. (2000), New Zealand Veterinary Journal, 48: 65-69. Title, "Isolation of *Helicobacter mustelae* from ferrets in New Zealand".
42. Spranger et al. (2005), Br. Nutr., 93 (6):765-71.
43. Garbom et al. (2004), Infect Immun., 72(3): 1333-1340.
44. Tschop et al. (2000) Nature, 407:908-13.
45. Choi et al. (2003), Edocrinology, 144 (3).
46. Remington's Pharmaceutical Sciences, $20^{th}$ edition, Mack Publishing Company.
47. Jones et al. (2005) Nat. Med. 11 (7): 786-90.

What is claimed is:

1. A composition comprising a *Helicobacter* cell comprising a nucleic acid comprising:
   (a) at least one non-*Helicobacter* sequence encoding a non-*Helicobacter* pharmacologically active molecule of interest linked to a secretory signal peptide; and
   (b) a regulatory sequence selected from the group consisting of *Helicobacter pylori* histidine kinase HP165 promoter, and FlaB sigma 54 promoter, wherein the regulatory sequence is capable of controlling expression of the non-*Helicobacter* sequence in the *Helicobacter* cell;
   wherein the *Helicobacter* cell is not a DapE mutant strain.

2. The composition of claim 1, wherein said *Helicobacter* cell is a *Helicobacter pylori* cell.

3. A composition comprising a *Helicobacter pylori* cell comprising a nucleic acid comprising:
   (a) a sequence encoding a fusion protein comprising a non-*Helicobacter* pharmacologically active molecule of interest operably linked to
   (b) an inducible promoter sequence selected from the group consisting of *Helicobacter pylori* histidine kinase HP165 promoter and FlaB sigma 54 promoter;
   wherein the *Helicobacter pylori* cell is not a DapE mutant strain.

4. The composition of claim 3, wherein the sequence is in a plasmid vector.

5. A pharmaceutical composition comprising as an active ingredient the composition of claim 4 together with a pharmaceutically acceptable diluent, carrier, adjuvant or combination thereof.

6. The composition of claim 3, wherein said *Helicobacter pylori* further comprises a second nucleic acid molecule encoding an immunomodulatory polypeptide.

7. The composition of claim 2, wherein the *Helicobacter pylori* cell is *Helicobacter pylori* strain 26695.

8. The composition of claim 1, further comprising an adjuvant.

9. The composition of claim 1, wherein the *Helicobacter* cell is an attenuated *Helicobacter* cell.

10. The composition of claim 1, wherein the *Helicobacter* cell is non-invasive.

11. The composition of claim 1, wherein the *Helicobacter* cell is non-pathogenic.

12. The composition of claim 1, wherein the regulatory sequence is the *Helicobacter pylori* histidine kinase HP 165 promoter.

13. The composition of claim 1, wherein the regulatory sequence is the FlaB sigma 54 promoter.

14. A pharmaceutical composition comprising as an active ingredient the composition of claim 1 together with a pharmaceutically acceptable carrier, adjuvant, or combination thereof.

15. The composition of claim 3, wherein the *Helicobacter pylori* cell is *Helicobacter pylori* strain 26695.

16. The composition of claim 3, further comprising an adjuvant.

17. The composition of claim 3, wherein the *Helicobacter pylori* cell is an attenuated *Helicobacter pylori* cell.

18. The composition of claim 3, wherein the *Helicobacter pylori* cell is non-invasive.

19. The composition of claim 3, wherein the *Helicobacter pylori* cell is non-pathogenic.

20. The composition of claim 3, wherein the fusion protein comprises a *Helicobacter* sequence.

21. The composition of claim 3, wherein the fusion protein comprises a surface layer protein sequence.

22. The composition of claim 21, wherein the surface layer protein is HopE.

23. A composition comprising a *Helicobacter pylori* cell comprising a nucleic acid comprising:
   (a) a sequence encoding a fusion protein comprising a non-*Helicobacter* pharmacologically active molecule of interest, wherein the fusion protein comprises a HopE surface layer protein sequence, operably linked to
   (b) an inducible promoter sequence;
   wherein the *Helicobacter pylori* cell is not a DapE mutant strain.

24. The composition of claim 23, wherein the sequence is in a plasmid vector.

25. A pharmaceutical composition comprising as an active ingredient the composition of claim 23 together with a pharmaceutically acceptable diluent, carrier, adjuvant or combination thereof.

26. The composition of claim 23, wherein said *Helicobacter pylori* further comprises a second nucleic acid molecule encoding an immunomodulatory polypeptide.

27. The composition of claim 23, wherein the *Helicobacter pylori* cell is *Helicobacter pylori* strain 26695.

28. The composition of claim 23, further comprising an adjuvant.

29. The composition of claim 23, wherein the *Helicobacter pylori* cell is an attenuated *Helicobacter pylori* cell.

30. The composition of claim 23, wherein the *Helicobacter pylori* cell is non-invasive.

31. The composition of claim 23, wherein the *Helicobacter pylori* cell is non-pathogenic.

32. The composition of claim 23, wherein the inducible promoter is an arabinose inducible promoter.

33. The composition of claim 23, wherein the inducible promoter is the promoter from the *Helicobacter pylori* histidine kinase HP 165.

34. A composition comprising a *Helicobacter pylori* cell comprising a nucleic acid comprising:
   (a) a sequence encoding a fusion protein comprising a non-*Helicobacter* pharmacologically active molecule of interest, wherein the fusion protein comprises a HopE surface layer protein sequence, operably linked to
   (b) an arabinose inducible promoter;
   wherein the *Helicobacter pylori* cell is not a DapE mutant strain.

35. The composition of claim 34, wherein the sequence is in a plasmid vector.

36. A pharmaceutical composition comprising as an active ingredient the composition of claim 35 together with a pharmaceutically acceptable diluent, carrier, adjuvant or combination thereof.

37. The composition of claim 34, wherein said *Helicobacter pylori* further comprises a second nucleic acid molecule encoding an immunomodulatory polypeptide.

38. The composition of claim 34, wherein the *Helicobacter pylori* cell is *Helicobacter pylori* strain 26695.

39. The composition of claim 34, further comprising an adjuvant.

40. The composition of claim 34, wherein the *Helicobacter pylori* cell is an attenuated *Helicobacter pylori* cell.

41. The composition of claim 34, wherein the *Helicobacter pylori* cell is non-invasive.

42. The composition of claim 34, wherein the *Helicobacter pylori* cell is non-pathogenic.

43. The composition of claim 34, wherein the fusion protein comprises a *Helicobacter* sequence.

* * * * *

UNITED STATES PATENT AND TRADEMARK OFFICE
CERTIFICATE OF CORRECTION

PATENT NO. : 7,968,324 B2
APPLICATION NO. : 11/202249
DATED : June 28, 2011
INVENTOR(S) : Barry J. Marshall It is certified that error appears in the above-identified patent and that said Letters Patent is hereby corrected as shown below:

On the First Page, Column 2 (Other Publications), line 2, delete "Escherichla" and insert
-- Escherichia --

On the First Page, Column 2 (Other Publications), line 6, delete "Fluoresent" and insert
-- Fluorescent --

On the First Page, Column 2 (Other Publications), line 12, delete "Philosopy," and insert
-- Philosophy, --

Signed and Sealed this
Sixteenth Day of August, 2011

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 7,968,324 B2 | Page 1 of 1 |
| APPLICATION NO. | : 11/202249 | |
| DATED | : June 28, 2011 | |
| INVENTOR(S) | : Marshall | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 198 days.

Signed and Sealed this
Twentieth Day of December, 2011

David J. Kappos
*Director of the United States Patent and Trademark Office*

SEQUENCE LISTING

```
<160> NUMBER OF SEQ ID NOS: 10

<210> SEQ ID NO 1
<211> LENGTH: 2796
<212> TYPE: DNA
<213> ORGANISM: Helicobacter pylori

<400> SEQUENCE: 1
gtcatgcgcg ttgtttttaa ttacatttta aacaacttgt tgttgttttt acatgtttta      60
ctcgcatgcg cgcgcgtgag ggattggggg ttgcaacccc ctaaataacg aagctgtagg     120
gtttctcatt tttgtggtga aaatgaataa aacagaactt cttgccaaca ctaacagaac     180
ttcttgccaa cactaacaga acttcttgcc aacactaaca gaacttcttg ccaacactaa     240
cagaacttct ttattttaaa gttatgatta ttaacaattt ttagacataa taacagcgtg     300
tgaagatact tttgtagcgg tatttcctat gtgcggcaaa atttggagca attagcttga     360
cttggttgag ttagtgggtt ggaggataga gagggcgaca cctcgttagg aggtatcaat     420
gtgaaagtat ttgtcgtatt agttctagta ttagtaattc tcgcacaatt gctatattag     480
gcttattcgt ggtctaaccc cttgtttatg ggggttggct cgttataagc atactgatac     540
gatcacactt attatacacc aaaagataag gagtatagag tggaatttga tcaatcagat     600
ttacaaaaag cgttgaaaat attagataca ctcccacaaa ccccacaaat tgagctacaa     660
aaacaagaaa tacaaaaccg catcaacaaa ataacagaga caatcattaa agaattacta     720
tcaaagcatg aaatcaagaa agaagaacta gaacccactc taaccccaaa acccacacca     780
ctcaaagagc cacaaaccac cccaacacca tgcaaagatt tagtggttag caccccctaaa    840
```

```
gataaaacct aatatcacct accacaataa cgctaataag gtcaatctag ggaaattgag      900
cgaaagggaa gccaatcttt tattcgctat ttttcaaaaa ctcaaagccc aagggaatac      960
cctcattcgt tttgaaccgc aagatttgaa acgcatgcta aacatagata tttctaatga     1020
gcgcttatca gaagtcgtta ttaagctgtg ggatagcatt aaaaccgctg atttttggaa     1080
aattagcgaa accgaaactt caatcattca agaaaattac atgctttta gtcggtgtaa     1140 aattgaattg aacaaaccga gtaaagattt gaagtattta gaaatccaac tcaacgataa     1200
ctatcaagac ttactcaaca atctgggcat gggtcaatac acttctttca atctgttaga     1260
atttcaaaga gtgagggta aatacgctaa acgctctat cgcttgctca agcaatacaa      1320
aagcacaggg attttgagcg tggaatggac tcaattcagg gagcttttag acattccaaa     1380
agactacaaa atggaaaaca tcgatcaaaa agtcttaacc ccctctctca aagaactcag     1440
aaaaatctac ccttttgaac acttgagcta taaaaaagaa cgcaaaagcc attacaagcg     1500
caaagtaacc cacattgatt tttattttga gcaatttcct taaggcgaaa ataagaaaca     1560
aaacaaagcc gacaagcaac gcgctcaaag ggacatcaag cttgtagcat gggatattca     1620
caaccaaatc gctaaaagaa acgcaaaagc cactatggaa gctaggtttc ttgaattgaa     1680
aactttgatc ggctatcagt tcaggaacaa tgacagtagg aacaaattaa agattgacaa     1740
caccactttt gaaagaatca atgtatttta catgtatctt aaccctaaaa ataagcataa     1800
cccccaaaaa ttccttgtat ccaacaagac attcgcattg gaactactat atatcaatag     1860
atacagccta aaaaaagac aacttgctag aagaatttaa ccccccaaaa tccaccctat     1920
caccaacgaa cctatcaagg aatttgcaga atacatcggc aaaacgatta acatcaccaa     1980
cttcaatgtg gatcaatgcc atgagggaat cagcaactac ctgacaatca ctaggatcgt     2040
gaactggacg taatcggatc tgtatttggt ccagatgtgg ataagcctgg gacttctcaa     2100
gcctttcatt gctaaagtga gaaaatttgg ggattggttc aagaacacta caggtgaaaa     2160
gacagatgca tgctgactaa actcatagaa aaactgaatc acgaaagaaa gaatgcaagc     2220
agaaaacaaa cacctaaaag aacaaggact agaaaaaatc tacactcaaa aagactacga     2280
gcagttaaaa gaacagcatt tgaaagaaat tgaagcactc aaaaaagaaa tccaaaaaac     2340
caagcaagaa acatacacgc aaccaaaaga atgtagccat ttagcgcatt cttttagccc     2400
taattcattc tttcaatcaa aatccgacta attcatcggc taaacgctaa aaatcgctta     2460
aaacgaaaaa tacaaagcaa aaaacttcat tcccctttta gtcgttaacc atttagccaa     2520
tctaactagt ttagcatcta aaggcgaatc tatcttgtgt tagacatcca accttaccaa     2580
aaccgcagag cgagcttaag agagattcaa gcggttttgc acgattgttt gctgccaaga     2640
aaaccaacaa gcgaagtaag gcgcatagac aaaagcgcat cgcagtttga aagcgtaggc     2700
gtcagaagtg gtttgcgtta gaatcaaaca agatagcgca aacctggcgt taggctaaaa     2760 aaccccctaaa aactaaaacc ccaaaatatg tagtgc                              2796
```

<210> SEQ ID NO 2
<211> LENGTH: 2796
<212> TYPE: DNA
<213> ORGANISM: Helicobacter pylori

<400> SEQUENCE: 2

```
cagtacgcgc aacaaaaatt aatgtaaaat ttgttgaaca acaacaaaaa tgtacaaaat       60
gagcgtacgc gcgcgcactc cctaaccccc aacgttgggg gatttattgc ttcgacatcc      120
caaagagtaa aaacaccact tttacttatt ttgtcttgaa gaacggttgt gattgtcttg      180
```

```
aagaacggtt gtgattgtct tgaagaacgg ttgtgattgt cttgaagaac ggttgtgatt        240
gtcttgaaga aataaaattt caatactaat aattgttaaa aatctgtatt attgtcgcac        300
acttctatga aaacatcgcc ataaaggata cacgccgttt taaacctcgt taatcgaact        360
gaaccaactc aatcacccaa cctcctatct ctcccgctgt ggagcaatcc tccatagtta        420
cactttcata aacagcataa tcaagatcat aatcattaag agcgtgttaa cgatataatc        480
cgaataagca ccagattggg gaacaaatac ccccaaccga gcaatattcg tatgactatg        540
ctagtgtgaa taatatgtgg ttttctattc ctcatatctc accttaaact agttagtcta        600
aatgtttttc gcaacttttta taatctatgt gagggtgttt ggggtgttta actcgatgtt        660
tttgttcttt atgttttggc gtagttgttt tattgtctct gttagtaatt tcttaatgat        720
agtttcgtac tttagttctt tcttcttgat cttgggtgag attggggttt tgggtgtggt        780
gagtttctcg tgtttggtg gggttgtggt acgtttctaa atcaccaatc gtggggattt        840
ctattttgga ttatagtgga tggtgttatt gcgattattc cagttagatc cctttaactc        900
gctttccctt cggttagaaa ataagcgata aaaagttttt gagtttcggg ttcccttatg        960
ggagtaagca aaacttggcg ttctaaactt tgcgtacgat ttgtatctat aaagattact       1020
cgcgaatagt cttcagcaat aattcgacac cctatcgtaa ttttggcgac taaaaacctt       1080
ttaatcgctt tggctttgaa gttagtaagt tcttttaatg tacgaaaaat cagccacatt       1140
ttaacttaac ttgtttggct catttctaaa cttcataaat ctttaggttg agttgctatt       1200
gatagttctg aatgagttgt tagacccgta cccagttatg tgaagaaagt tagacaatct       1260
taaagtttct cactccccat ttatgcgatt tgcgagata gcgaacgagt tcgttatgtt       1320
ttcgtgtccc taaaactcgc accttacctg agttaagtcc ctcgaaaatc tgtaaggttt       1380
tctgatgttt tacctttgt agctagtttt tcagaattgg gggagagagt ttcttgagtc       1440
tttttagatg ggaaaacttg tgaactcgat attttttctt gcgttttcgg taatgttcgc       1500
gtttcattgg gtgtaactaa aaataaaact cgttaaagga attccgcttt tattctttgt       1560
tttgtttcgg ctgttcgttg cgcgagtttc cctgtagttc gaacatcgta ccctataagt       1620
gttggtttag cgattttctt tgcgttttcg gtgatacctt cgatccaaag aacttaactt       1680
ttgaaactag ccgatagtca agtccttgtt actgtcatcc ttgtttaatt tctaactgtt       1740
gtggtgaaaa ctttcttagt ttacataaat gtacatagaa ttgggatttt tattcgtatt       1800
gggggttttt aaggaacata ggttgttctg taagcgtaac cttgatgata tatagttatc       1860
tatgtcggat ttttttttctg ttgaacgatc ttcttaaatt gggggttttt aggtgggata       1920
gtggttgctt ggatagttcc ttaaacgtct tatgtagccg ttttgctaat tgtagtggtt       1980
gaagttacac ctagttacgg tactcccctta gtcgttgatg gactgttagt gatcctagca       2040
cttgacctgc attagcctag acataaaacca ggtctacacc tattcggacc ctgaagagtt       2100
cggaaagtaa cgatttcact ctttttaaacc cctaaccaag ttcttgtgat gtccactttt       2160
ctgtctacgt acgactgatt tgagtatctt tttgacttag tgctttcttt cttacgttcg       2220
tcttttgttt gtggattttc ttgttcctga tctttttttag atgtgagttt ttctgatgct       2280
cgtcaatttt cttgtcgtaa actttcttta acttcgtgag ttttttcttt aggttttttg       2340
gttcgttctt tgtatgtgcg ttggttttct tacatcggta aatcgcgtaa gaaaatcggg       2400
attaagtaag aaagttagtt ttaggctgat taagtagccg attttgcgatt tttagcgaat       2460 tttgcttttt atgtttcgtt ttttgaagta aggggaaaat cagcaattgg taaatcggtt       2520
agattgatca aatcgtagat ttccgcttag atagaacaca atctgtaggt tggaatggtt       2580
```

-continued

| | |
|---|---|
| ttggcgtctc gctcgaattc tctctaagtt cgccaaaacg tgctaacaaa cgacggttct | 2640 |
| tttggttgtt cgcttcattc cgcgtatctg ttttcgcgta gcgtcaaact ttcgcatccg | 2700 |
| cagtcttcac caaacgcaat cttagtttgt tctatcgcgt ttggaccgca atccgatttt | 2760 |
| ttggggattt ttgattttgg ggttttatac atcacg | 2796 |

<210> SEQ ID NO 3
<211> LENGTH: 3444
<212> TYPE: DNA
<213> ORGANISM: Helicobacter pylori

<400> SEQUENCE: 3

| | |
|---|---|
| tctacacaat taacaatctt tagctacaat aacagcgtgt gaagatgctt tcacagcggt | 60 |
| atttcctatg tgcggcaaaa tttggagcaa ttaacttgac ttggttgggt tagtgggttg | 120 |
| gaggatagag agggcgacac ctcgttagga ggtatcaatg tgaaagtatt tgtcgtatta | 180 |
| gttctagtat tagtaattct cgcacaattg ctatattagg cttatttgtg gtctaacccc | 240 |
| ttgtttatgg gggttagatc cttataagca tactgatacg atcacactta ttatacacca | 300 |
| aaagataagg agtatagagt ggaatttgat caattagaat cacaaagatc agacttacaa | 360 |
| aaagtgttaa aagaattaga tacactccca aaaccccac aaattgagct acaaaaacaa | 420 |
| gaaatacaaa accgcatcaa caaaataaca gacacaatca ttaagaatt actatcaaaa | 480 |
| catgaaatca aaaagaaga actagaaccc actctaaccc caaaaccac accaacaaaa | 540 |
| gagccacaaa ccaccccac accatgcaaa aatttagtgg ttagcacccc taaagataaa | 600 |
| acctatatca cctaccacaa taacgctaat aaggtcaatc tagggaaatt gagcgaaagg | 660 |
| gaagccaatc ttttattcgc tatttttcaa aggcttaaag atcaagggaa taccctcatt | 720 |
| cgttttgaac cgcaagattt aaaacgcatg atcatggtca aatccaactt aaccaacagg | 780 |
| caattattgc aagtcttaaa aaatttgctt gacaacatta gcggtgctaa ttttttggatc | 840 |
| aattagagag catgttgaaa atggcgaaat ctatgaagat cacactagct acatgctttt | 900 |
| caaacaattt gaaatccgca tccataagcc aacacaaact atagaatact tagatgtcca | 960 |
| actcaatgat agctatcaat acttgctcaa caatctagga atgggcggtc aatacacttc | 1020 |
| tttcaatctc ttagaatttc aaagggtgag gggcaaatag tgagagcgtt aaatttcccc | 1080 |
| ccccctattcc ccttaaaaag gacccttatc ccagggaatt tttggcccca atacaattag | 1140 |
| ggccaaaaac ccggtccctt ccatggctta accaacccaa ttgggggatt ccaatttccc | 1200 |
| ctggatggga ataacccaag gctttttttg aaaattccac ctaccatttg gtccaaaatt | 1260 |
| ggatggacaa ttccaaattc caaatcttct tttccaagaa tggggggccaa cccttgacaa | 1320 |
| actccttaaa cctttttcatt cggctaaaag gttgaaaaac atttggaaga tttggtttaa | 1380 |
| ggaaatattt atcgggtgaa aagaccagat gcatggctaa cttaaactcc atagaaaaac | 1440 |
| tgaatcacga aagaaagaat gctatcaaaa atggcattta ccacttgatc caaatcaaat | 1500 |
| tttcttacaa ctccaatcgc attgaaggaa gcggtttgac ttatgaacaa accgctcata | 1560 |
| tttttgacaa atccgttctc ataactgaaa aaaacaccaa tatcaaactt gatgatattt | 1620 |
| ttgaaactat caatcatttt gaatgcgtga attacttgct tgaaagctat aaagaacctt | 1680 |
| tgagtttaga atactttaag aatttacaca aaatcttgaa aaagaattgt tctgatgaag | 1740 |
| ttattggtga tttttaaaaaa cgccctaatt ttgtaggcaa tagcgccaca acaagaccca | 1800 |
| aattagttga aagcgaattg acaaatcttg tgaaaaatta tcaacgcaac cttgaagtga | 1860 |
| gtttgaaaaa caatatcatg cctttcatca tagaaaacga acacaaagcc ttttactaca | 1920 |

```
gggcatcaa agaatatgac aacacaaaag gctacttgaa agacaccatt ttgcaaagtc      1980
aagacaattt caatgaaatg gttagctatt tcttttcttg agtgaaaccg cttattttg      2040 cttgtgtgct tttgttttt gcgttttag ttgtaggtgg taagaaatat cggttttttg      2100
cttttcgttg gttgtaggcg attttagata gcaaaaaaca gctaaaaaat ccaagcaacc     2160
taattgattt caaaccaact tcatttccct tttagtcgtt agccatttag ccaatctaac     2220
tagtttagca tctaaaagcg catataactt gagttagcaa tccaaccaat actaaaaccg    2280
cctagcgaag cgttagcgag caaaataagc ggttttagac cgattgtttg ctgacaagca    2340
aacaccaata agcgagcgtt agcgagcatg acaaaagcg catcgcagtt tgaaagcgta     2400
ggcgttagcc gaagctgttt tgcgtaagca aatcaaacaa gatagcgcaa gccgaggtgc    2460
agcccaagaa tttgaattaa ccatgcggt gtttagggcg ttttagcgtg atcgctttat    2520
tacatgtttt aaacagcatg ctgtttttta catgttttac tcgcatgcgc gcgcgctagg    2580
tattggtggt tggaatagcc taaataacgc agctgtatgg tttctcattt ttcggtgaca    2640
atgaataagg ggtagttctt gcgagtcata agtgtagttc ttgcgagtca taagtgtagt   2700
tcttgcgagt cataagtgta gttcttgcga gtcataagtg tagttctctt cacaatatct   2760
acacaattca caatctctag ctacaataac agcgtgtgaa gatgctttca cagcggtatt   2820
tcctatgtgc ggcaaaattt ggagcaatta gcttttaaaag ctagtgggtt gggagtttgt 2880
agcgggtatg cactccgtta ggaggcacac catgaaagca ttttttgatag tagtgatttt    2940 agtggtaatc ttgacacagc cactatatta aaaccttagc gttttaataa ccctttataag   3000 tccgccaaga cttcttaagg gtttcactcc tgttattata tcgtctttg aaaaataagc    3060 attaaaaggc gcttaaatgc ccatgaatac gaattttgaa cagcttagaa aacaagaatt   3120
ggaattacga aaattattag aagaattaga aacgctccca caaaccccac aaattaaact    3180
gcaaaaacaa aaaatacaaa cttacataga caagataaca ccaagtattt tgagcggttt    3240
tgatcaaaaa ttcaaagaaa ttatagaaaa tctatcaaat gaatttgaaa agaaaaatc    3300 cacaccactc aaagagccac aaaccacccc cacaccatgc aaagatttag tggttagcac    3360
ccctaaagat aacacctata ccacctacca caataacgct aataaggtca atctagggaa   3420
attgagcgaa agggaagcca atct                                           3444
```

<210> SEQ ID NO 4
<211> LENGTH: 580
<212> TYPE: DNA
<213> ORGANISM: Hepatitis C virus

<400> SEQUENCE: 4

```
catgagcacg aatcctaaac ctcaaagaaa aaccaaacgt aacaccaacc gtcgcccaca      60
ggacgtcaag ttcccgggtg gcggtcagat cgttggtgga gtttacttgt tgccgcgcag    120
gggccctaga ttgggtgtgc gcgcgacgag gaagacttcc gagcggtcgc aacctcgagg    180
tagacgtcag cctatcccca aggcacgtcg gcccgagggc aggacctggg ctcagcccgg    240 gtaccccttgg cccctctatg gcaatgaggg ttgcgggtgg gcgggatggc tcctgtctcc    300
ccgtggctct cggcctagct ggggccccac agaccccggg cgtaggtcgc gcaatttggg    360
taaggtcatc gataccctta cgtgcggctt cgccgacctc atggggtaca taccgctcgt    420
cggcgcccct cttggaggcg ctgccagggc cctggcgcat ggcgtccggg ttctggaaga    480
cggcgtgaac tatgcaacag gaaccttcc tggttgctct ttctctatct tccttctggc     540
cctgctctct tgcctgactg tgcccgcttc agcctaccaa                          580
```

<210> SEQ ID NO 5
<211> LENGTH: 135
<212> TYPE: DNA
<213> ORGANISM: Hepatitis C virus

<400> SEQUENCE: 5
aatcctaaac ctcaaagaaa aaccaaacgt aacaccaacc gtcgcccaca ggacgtcaag    60
ttcccgggtg gcggtcagat cgttggtgga gtttacttgt tgccgcgcag gggccctaga   120
ttgggtgtgc gcgcg                                                    135

<210> SEQ ID NO 6
<211> LENGTH: 1108
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 6
atgccatagc attttatcc ataagattag cggatcctac ctgacgcttt ttatcgcaac     60
tctctactgt ttctccatac ccgttttttg ggctaacagg aggaattaac catggaattt   120
atgaaaaagt ttgtagcttt agggcttcta tccgcagttt taagctcttc gttgttagcc   180
gaaggtgatg gtgtttatat agggactaat tatcagcttg acaagcccg tttgaatagt    240 aatatttata atacagggga ttgcacaggg agtgttgtag gttgcccccc aggtcttacc   300
gctaataagc ataatccagg aggcaccaat atcaattggc atgctaaata cgctaatggg   360
gctttgaatg gtcttgggtt gaatgtgggt tataagaagt tcttccagtt caagtctttt   420
gatatgacaa gcaagtggtt tggttttaga gtgtatgggc tttttgatta tgggcatgcc   480
actttaggca agcaagttta tgcacctaat aaaatccagt tggatatggt ctcttgggt    540 gtggggagcg atttgttagc tgatattatt gataacgata acgcttcttt tggtattttt   600
ggtggggtcg ctatcggcgg taacacttgg aaaagctcag cggcaaacta ttggaaagag   660
caaatcattg aagctaaggg tcctgatgtt tgtaccccta cttattgtaa ccctaacgct   720
ccttatagca ccaaaacttc aaccgtcgct tttcaggtat ggttgaattt tgggggtgaga  780 gccaatattt acaagcataa tggcgtagag tttggcgtga gagtgccgct actcatcaac   840 aagttttga gtgcgggtcc taacgctact aatctttatt accatttgaa acgggattat    900
tcgctttatt tagggtataa ctacactttt tctcgagatc tgcagctggt acgatatggg   960
aattcgaagc tttctagaac aaaaactcat ctcagaagag gatctgaata gcgccgtcga  1020
ccatcatcat catcattgag tttaacggtc tccagcttgg ctgttttggc ggatgagaga  1080
agattttcag cctgatacag attaaatc                                    1108

<210> SEQ ID NO 7
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
aaggatccga taggaatgta aaggaatgg                                      29

<210> SEQ ID NO 8
<211> LENGTH: 28

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
ccgaattcta aaggcatgaa cgcttgca                                          28

<210> SEQ ID NO 9
<211> LENGTH: 15
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
agatctaagg acgtc                                                        15

<210> SEQ ID NO 10
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 10

His His His His His His
  1               5
```